US007138431B1

(12) United States Patent
Chilton

(10) Patent No.: US 7,138,431 B1
(45) Date of Patent: Nov. 21, 2006

(54) DIETARY CONTROL OF ARACHIDONIC ACID METABOLISM

(75) Inventor: Floyd H. Chilton, Pilot Mount, NC (US)

(73) Assignee: Wake Forest University, Winston-Salem, NC (US)

( * ) Notice: Subject to any disclaimer, the term of this patent is extended or adjusted under 35 U.S.C. 154(b) by 0 days.

(21) Appl. No.: 09/644,380

(22) Filed: Aug. 23, 2000

Related U.S. Application Data

(63) Continuation-in-part of application No. PCT/US99/03120, filed on Feb. 12, 1999, which is a continuation-in-part of application No. 09/028,256, filed on Feb. 23, 1998, now Pat. No. 6,107,334.

(51) Int. Cl.
*A61K 31/185* (2006.01)
*A61K 31/20* (2006.01)
*A61K 47/00* (2006.01)

(52) U.S. Cl. ......................... 514/558; 514/557; 426/72; 424/439

(58) Field of Classification Search ................ 514/553, 514/558, 557; 426/72; 424/439
See application file for complete search history.

(56) References Cited

U.S. PATENT DOCUMENTS

| | | | |
|---|---|---|---|
| 4,154,863 A | * | 5/1979 | Kahn et al. |
| 4,309,415 A | | 1/1982 | Horrobin |
| 4,386,072 A | | 5/1983 | Horrobin et al. |
| 4,444,755 A | | 4/1984 | Horrobin |
| 4,560,514 A | | 12/1985 | Samuelsson et al. |
| 4,576,758 A | | 3/1986 | Morris |
| 4,666,701 A | | 5/1987 | Horrobin et al. |
| 4,758,592 A | | 7/1988 | Horrobin et al. |
| 4,888,326 A | | 12/1989 | Horrobin |
| 4,954,638 A | | 9/1990 | Young et al. |
| 4,965,075 A | | 10/1990 | Horrobin et al. |
| 4,977,187 A | | 12/1990 | Horrobin |
| 5,141,958 A | | 8/1992 | Crozier-Willi et al. |
| 5,158,975 A | | 10/1992 | Guichardant et al. |
| 5,178,873 A | | 1/1993 | Horrobin et al. |
| 5,223,285 A | | 6/1993 | DeMichele et al. |
| 5,328,691 A | | 7/1994 | Horrobin et al. |
| 5,336,496 A | | 8/1994 | Akimoto et al. |
| 5,352,700 A | | 10/1994 | Frithz et al. |
| 5,411,988 A | | 5/1995 | Bockow et al. |
| 5,508,307 A | | 4/1996 | Horrobin et al. |
| 5,516,801 A | | 5/1996 | Horrobin et al. |
| 5,562,913 A | | 10/1996 | Horrobin |
| 5,683,898 A | | 11/1997 | Yazawa et al. |
| 5,734,034 A | | 3/1998 | Jayasena et al. |

FOREIGN PATENT DOCUMENTS

| | | |
|---|---|---|
| EP | 0 598 365 A1 | 5/1994 |
| EP | 0 598 365 B1 | 5/1994 |
| EP | 0 711 503 A2 | 5/1996 |
| EP | 0 713 653 A1 | 5/1996 |
| EP | 782827 * | 7/1997 |
| WO | WO 9602488 A1 | 2/1996 |
| WO | WO 96/31457 | 10/1996 |
| WO | WO 97/21434 | 6/1997 |
| WO | WO 9816216 A1 | 4/1998 |

OTHER PUBLICATIONS

Obukowicz, et al., "Identification and Characterization of a Novel Δ6/Δ5 Fatty Acid Desaturase Inhibitor As a Potential Anti-Inflammatory Agent," 55:1045-58, 1998.
Palombo, et al., "Metabolic Support: Cyclic vs Continuous Enternal Feeding With ω-3 and γ-Linolenic Fatty Acids: Effects on Modulation of Phospholipid Fatty Acids in Rat Lung and Liver Immune Cells," Journal of Parenteral and Enternal Nutrition, 21(3):123-132, May 1996.
Dialog Search Patent Family printed Jun. 3, 1998.
Byars et al., "Black Currant Seed Oil as a Source Polyunsaturated Fatty Acids in the Treatment of Inflammatory Disease," (Abstract) Biochem. Soc. Trans. 20(12), 139s, 1992.
Rothman et al., "Effects of Unsaturated Fatty Acids on Interleukin-1.Beta Production by Human Monocytes," (Abstract) Cytokine, 9(12):1008-12, 1997.
International Search Report, PCT/US99/03120, Jun. 24, 1999.
Nasser et al. *The Influence of Dietary Manipulation with n-3 and n-6 Fatty Acids on Liver and Plasma Phospholipid Fatty Acids in Rats.* Lipids, vol. 21 (10), 1986, pp. 652-656.
Nasser et al. *Response of Tissue Phospholipid Fatty Acid Composition to Dietary (n-6) and Replacement with Marine (n-3) and Saturated Fatty Acids in the Rat.* Nutrition Research, vol. 6, 1986, pp. 1397-1409.
Takahashi et al. *Effect of Different Ratios of Dietary N-6 and N-3 Fatty Acids on Fatty Acid Composition, Prostaglandin Formation and Platelet Aggregation in the Rat.* Thrombosis Research, vol. 47, 1987, pp. 135-146.
Horrobin et al. *Clinical Biochemistry of Essential Fatty Acids.* Omega-6 Essential Fatty Acids: Pathophysiology and Roles in Clinical Medicine, 1990, pp. 21-53.
Huang et al. *Modulation of Tissue Fatty Acid Composition, Prostaglandin Production and Cholesterol Levels by Dietary Manipulation of n-3 and n-6 Essential Fatty Acid Metabolites.* Omega-6 Essential Fatty Acids: Pathophysiology and Roles in Clinical Medicine, 1990, pp. 127-144.
Zurler et al. *Anti-Inflammatory Effects of γ-Linolenic Acid: Studies in Animals and in Cultured Cells.* Omega-6 Essential Fatty Acids: Pathophysiology and Roles in Clinical Medicine, 1990, pp. 203-221.
Third party observations submitted by Reddie & Grose in European Application No. 99906992.5 (Feb. 14, 2002).

* cited by examiner

*Primary Examiner*—Sreeni Padmanabhan
*Assistant Examiner*—Jennifer Kim
(74) *Attorney, Agent, or Firm*—Myers Bigel Sibley & Sajovec, PA

(57) ABSTRACT

Compositions for the treatment of symptoms of inflammatory disorders may include gamma-linolenic acid or dihomogammalinolenic acid, an inhibitor of $\Delta^5$ desaturase, and optionally stearidonic acid or ω-3 arachidonic acid. Preferred formulations may be in the form of a good tasting, preferably milk or fruit based drink, or a dried powder. Compositions reduce inflammation and inhibit increase in serum arachidonic acid associated with gamma-linolenic acid.

4 Claims, 13 Drawing Sheets

DIETARY CONTROL OF ARACHIDONIC ACID METABOLISM

CROSS REFERENCE TO RELATED APPLICATIONS

The present application is a continuation-in-part of PCT/US99/03120, filed Feb. 12, 1999, which is a continuation-in-part of U.S. Ser. No. 09/028,256, filed Feb. 23, 1998, now U.S. Pat. No. 6,107,334.

FIELD OF THE INVENTION

The present invention relates generally to the fields of lipid metabolism and dietary supplementation. More particularly, it concerns compositions and methods for controlling or reducing symptoms of inflammation or inflammatory conditions that include the use of unsaturated fatty acids, unsaturated fatty acid precursors, and/or unsaturated fatty acid analogs in nutritional supplements.

DESCRIPTION OF RELATED ART

Arachidonic acid (AA) is a polyunsaturated fatty acid found in relatively small quantities in membranes of mammalian cells. Research over the last four decades has shown that the in vivo modulation of levels of arachidonic acid and oxygen-containing derivatives of arachidonic acid (known as eicosanoids) is intimately liked to human disease (for a review, see Samuelsson et al., Science, 237:1171–1176, 1987 and Chilton et al., In: Crystal, West and Barnes, eds., Lung: Scientific Foundations, Lippincott-Raven Publishers, Chapter 6, 77–88, 1997). For example, during inflammation, low levels of certain arachidonic acid derivatives render a protective response leading to enhanced disease resistance. However, these same molecules induce an autotoxic response leading to a variety of inflammatory disorders when produced in excessive quantities. Over the past three decades, the therapeutic utility of blocking the metabolism of arachidonic acid through multiple pathways including 5-lipoxygenase and cyclooxygenase I and II has become evident for the treatment of a wide range of inflammatory disorders.

Since arachidonic acid or its precursors found in cells and tissues must be derived from diets, it follows that diet may affect diseases controlled by arachidonic acid or its derivatives. This relationship was suggested in the 1960s by studies which showed differences in frequencies of inflammatory disorders among Greenland Eskimos and Danes (Chilton et al., Biochim. Biophys. Acta, 1299:1–15, 1996; Dyerberg and Bang, Lancet, ii:443435, 1979). Later studies showed similar differences between Japanese and Americans. These differences (Danes and Americans have much higher frequencies of inflammatory disorders including asthma, arthritis, psoriasis and acute myocardial infarction) were attributed, in large part, to the consumption by Danes and Americans, on Western diets, of high dietary quantities of precursor fatty acids of arachidonic acid (termed n-6 fatty acids) and arachidonic acid, offset by the low consumption of n-3 fatty acids.

Based on these observations, a number of dietary fatty acid reduction and supplementation strategies were undertaken in an attempt to influence arachidonic acid metabolism, eicosanoid production and clinical outcomes. These studies carried out over the last two decades have revealed that controlling dietary fatty acid intake in a number of animal models has great potential in reducing eicosanoid synthesis and ameliorating inflammation in models which mimic human arthritis, asthma, or glomerulonephritis (Prickett et al., J. Clin. Invest., 68:556–559, 1981; Kelley et al., J. Immunol., 134:1914–1919, 1985; Lefkowith et al., J. Immunol., 145:1523–1529, 1990; Rovin et al., J. Immunol., 145:1238–1245, 1990; Hurd et al., J. Clin. Invest., 67:476–482, 1981).

These studies demonstrated that the formation of derivatives of AA and the subsequent effects of these compounds (eicosanoids) on cells and tissues are central processes in inflammation and allergy. Dietary fatty acid reduction and supplementation strategies have been utilized in animals and humans in an attempt to modulate cellular AA levels and metabolism, and to ameliorate clinical inflammatory disorders. However, dietary modifications in humans on Western diets have shown only modest efficacy. If these observations are to prove useful in the treatment of such disorders, it is necessary to find more efficient dietary strategies to reduce eicosanoid generation in humans and to determine the mechanism(s) leading to this reduction.

In terms of inflammation, at least four dietary reduction and supplementation strategies have been utilized in both animals and humans in an attempt to influence eicosanoid production and clinical outcomes. One strategy has been to supplement "normal" diets with n-3 fatty acids. Here, there has been some controversy as to how effective these fatty acids are in reducing lipid mediators (eicosanoids) of inflammation (Chilton et al., J. Clin. Invest., 91:115–122, 1993; Sperling et al., J. Immunol., 139:41864191, 1987; Strasser et al., Proc. Natl. Acad. Sci. USA, 82:1540–1543, 1984; Kojima et al., Dermatologica, 182:225–230, 1991; Galloway et al., Clin. Sci., 68:449454, 1985; Mori et al., Lipids, 22:744–750, 1987; Ahmed and Holub, Lipids, 19:617–724, 1984; Payan et al., J. Clin. Immunol., 6:402–410, 1986; Rosenthal and Hills, Biochem. Biophys. Acta, 875:382–391, 1986; Triggiani et al., J. Immunol., 145:2241–2248, 1990). For example, several studies report only modest inhibition of leukotrienes and PAF after n-3 fatty acid supplementation, while other investigations report more dramatic reductions (Chilton et al., 1993; Sperling et al., 1987; Strasser et al., 1984). The basis for these discrepancies is unclear at this time. In addition to eicosanoids, n-3 fatty acids have been shown to affect processes such as gene expression, cytokine generation and programmed cell death in a number of in vitro and in vivo settings (Endres et al., N. Engl. J. Med., 320:265–271, 1989; Clarke and Jump, Lipids, 31:87-S 11, 1996; Chandrasekar et al., J. Autoimmunity, 8:381–393, 1995; Fernandes et al., J. Immunol., 152:5979–5987, 1994).

A second strategy to effect changes in AA metabolism in humans has been to remove dietary essential fatty acids from the diet. This eliminates sources of cellular AA that are derived from dietary linoleic acid (LA). Severe restrictions of LA intake in infants result in significant falls in levels of prostaglandin metabolites (Friedman et al., Pediat. Res., 12:711–714, 1978). Wene and colleagues studied healthy men on fat-free eucaloric diets and found that LA levels in serum components fell dramatically within seven days of starting the diet (Wene et al., J. Clin. Invest., 56:127–34, 1975). However, if calorie intake was then reduced (intermittent fasting), LA levels in serum increased. This LA repletion may be due to mobilization of fatty acids from adipose tissue triglycerides.

A third strategy to reduce AA metabolism has been to restrict preformed AA in diets of humans. There are several conflicting studies in humans restricting preformed AA by the chronic avoidance of animal tissue with results varying from increases to moderate reductions in serum AA levels (Phinney et al., *Am. J. Clin. Nutr.*, 51:385–392, 1990; Sanders et al., *Am. J. Clin. Nutr.*, 31:805–813, 1978; Melchert et al., *Atheroscler.*, 65:159–166, 1987). In contrast to studies restricting 120 dietary AA, humans supplemented with AA (an additional 6 g/day) exhibit a pronounced increase in AA levels within plasma triglycerides, phospholipids, cholesterol esters, and platelet phospholipids (Seyberth et al., *Clin. Pharmacol. Ther.*, 18:521–529, 1975). This increase within complex lipids is accompanied by an increase in eicosanoid generation and a marked decrease in the ADP threshold dose required to induce platelet aggregation.

A fourth strategy that has been utilized to influence AA metabolism is to supplement normal diets with oils (primrose and borage) rich in gamma linolenic acid (18:3, n-6). Such oils have been shown to improve clinical symptoms of patients with atopic dermatitis and rheumatoid arthritis (Leventhal et al., *Ann. Intern. Med.*, 119:867–873, 1993; Miller et al., *J. Nutr.*, 120:36–44, 1990; Horrobin, *J. Lipid Res.*, 31:163–194, 1992; Zibok and Fletcher, *Am J. Clin. Nutr.*, 55:39–45, 1992; Tate et al., J. Rheum., 16:729–734, 1989). The mechanisms by which GLA influences these inflammatory disorders has not been elucidated. In fact, it is paradoxical that providing a dietary precursor of AA, GLA, attenuates inflammation. It is known that a portion of the GLA provided is elongated (by 2 carbons) in vivo to form dihomogammalinolenic acid (DGLA) (Horrobin, 1992; Zibok and Fletcher, 1992; Tate et al., 1989). DGLA can then be metabolized to oxygenated products, 15-OH-20:3. (15 HETrE) and prostaglandin E, by 15 lipoxygenase and cyclooxygenase, respectively (Miller et al., 1990; Horrobin, 1992). $PGE_1$ has been found to be anti-inflammatory in a variety of in vitro systems and animal models (Kerins et al., *Prog. Hemostasis Thromb.*, 10:307–337, 1991). GLA supplementation also has been shown to reduce the capacity of some cells to produce AA-derived eicosanoids (Leventhal et al., 1993; Zibok and Fletcher, 1992).

The inventor's laboratory has provided humans on controlled diets with a wide range of dietary fatty acid supplements and supplement combinations in an attempt to affect AA metabolism in humans (Chilton et al., 1993; Triggiani et al., 1990; Chilton-Lopez et al., *J. Immunol.*, 156:2941–2947, 1996; Johnson et al, *J. Nutr.*, 127:1435–1444, 1997). In these studies, well defined diets (prepared and fed in a General Clinical Research Center [GCRC]) and measurement techniques (negative ion chemical ionization GC/MS) that precisely determine fatty acid and eicosanoid levels in serum and inflammatory cells have been utilized.

Although much work has been performed on the dietary supplementation of fats, many questions remain to be answered, including the determination of the capacity of different inflammatory cells to synthesize (elongate and desaturate) polyunsaturated fatty acids; the major mechanism(s) by which analogs (which can be induced by dietary supplementation) of AA influence eicosanoid generation and the development of dietary strategies that will produce natural antagonists of AA in inflammatory cells, thereby reducing the synthesis of pro-inflammatory eicosanoids without increasing serum levels of AA. These and other questions are at least partially addressed by the present disclosure.

SUMMARY OF THE INVENTION

The present invention is directed to dietary strategies that treat, or reduce the side effects of inflammatory disorders such as asthma and arthritis. Although GLA has been reported as beneficial in reducing symptoms of certain inflammatory conditions, unfortunately, dietary supplementation with GLA results in an increase in serum arachidonic acid (AA), with potentially undesirable effects. In studies disclosed herein, however, it is shown that GLA supplementation does not increase AA in certain inflammatory cells. Also as disclosed herein, neutrophils, the inflammatory response cells, do not possess a $\Delta^5$ desaturase activity, as do hepatocytes. Thus, the product of GLA elongation, DGLA cannot be converted to AA and eicosanoids in inflammatory cells. In serum, however, DGLA formed from the elongation of GLA is converted to AA via the action of a $\Delta^5$ desaturase. This build-up of serum AA is likely to have harmful consequences in humans. For example, previous studies have demonstrated that increases in AA of this magnitude can increase platelet reactivity, which is undesirable in most cases.

As disclosed herein, these potentially harmful effects can be circumvented by providing a $\Delta^5$ desaturase inhibitor in combination with the GLA, thus preventing the increase in serum AA levels upon GLA administration. In addition, stearidonic acid or ω-3 arachidonic acid may be provided as antagonists of arachidonic acid metabolism in immune cells, because, as shown herein, stearidonic acid is taken up by human neutrophils and elongated to ω-3 arachidonic acid, also a competitive inhibitor of arachidonic acid metabolism. It is contemplated that a buildup of ω-3 arachidonic acid in neutrophils may also result in further inhibition of the serum $\Delta^5$ desaturation of DGLA in hepatocytes, resulting in further inhibition of serum arachidonic acid accumulation.

Described herein are compositions for diminishing symptoms of inflammatory disorders. The compositions include γ-linolenic acid or dihomogammalinolenic acid, $\Delta^5$ desaturase inhibitors, and ω-3 competitive inhibitors of arachidonic acid metabolism. In preferred embodiments the described ingredients include from around 80% to about 95% pure polyunsaturated fatty acids. Preferred $\Delta^5$ desaturase inhibitors include eicosapentaenoic acid, sesamin, episesamin, sesaminol, sesamolin, curcumin, α-linolenic acid, heneicosapentaenoic acid, docosahexaenoic acid, alkyl gallate, propyl gallate, and p-isopentoxyaniline. These inhibitors may be provided as free fatty acids, fatty acyl esters, diglycerides, triglycerides, ethyl esters, phospholipids, steryl esters, sphingolipids, or a combination of these. In certain embodiments, a competitive inhibitor of arachidonic acid metabolism may be ω-3 arachidonic acid or stearidonic acid. In certain embodiments a competitive inhibitor of inflammatory cell AA metabolism and liver $\Delta^5$ desaturase may be ω-3 AA or stearidonic acid (SA).

Preferred formulations of the disclosed compositions include flavored liquids or powders that may be rehydrated to form a drink. Preferred formulations may also include ingredients such as water, corn syrup, maltodextrin, sodium caseinate, calcium caseinate, soy protein, magnesium chloride, potassium citrate, calcium phosphate tribasic, or soy lecithin. The disclosed formulations may also include various emulsifying or stabilizing agents and antioxidants known in the art. Suitable emulsifying or stabilizing agents include, without limitation, xanthan gum, guar gum, pectin, carob seed gum (locust-bean gum), tragacanth gum, methylcellulose, alginates, carrageenan or the like. Additional preferred ingredients may include sucrose, glucose, aspartame, glycerol, sorbitol, sorbic acid, galactolipids, sphingolipids, lecithins, cellulose, hydroxypropylmethylcellulose, malt or malt extract, gelatin, casein, cholesterol, egg yolk, sodium dodecyl sulfate, benzalkonium chloride, p-hydroxybenzoic acid, vitamin C, vitamin E or alpha-tocopherol. A composition in the form of a dried powder may be prepared using any suitable pharmaceutical carrier(s) routinely used for preparing solid formulations. Examples of such carriers include magnesium stearate, starch, lactose, sucrose and cellulose.

In certain embodiments, the disclosed compositions are contained in an essentially oxygen-free, air-tight container. By oxygen-free is meant the ambient air trapped within the container is essentially free of oxygen as is achieved, for example, by sealing the container in an oxidatively inert gas environment, such as a nitrogen gas environment. Preferred containers include cans or foil pouches that provide a punch-through opening for a straw. The compositions may also include a flavoring agent such as a fruit flavoring agent or a fruit juice. Other flavoring agents may include vanilla, chocolate, eggnog, berry, or other flavoring agents known in the art. Preferred antioxidants include beta-carotene, vitamin E, vitamin C, selenium, alpha tocopherol, and taurine.

Certain compositions disclosed herein may be described as milk based drinks for treatment of inflammatory disorders that may include an unsaturated fatty acid portion containing γ-linolenic acid or dihomogammalinolenic acid, a $\Delta^5$ desaturase inhibitor, and stearidonic acid or ω-3 arachidonic acid. Alternatively, certain compositions, disclosed for treatment of an inflammatory disorder, may include γ-linolenic acid or dihomogammalinolenic acid, eicosapentaenoic acid, and stearidonic acid or ω-3 arachidonic acid. Such formulations may be used in the treatment of asthma, allergic rhinitis, allergic rhinoconjunctivitis, psoriasis, acute myocardial infarction, glomerulonephritis, Crohn's disease, inflammatory bowel disease, or arthritis, for example. The compositions are also effective for treatment of conditions that have an inflammatory component that includes a role for arachidonic acid metabolites, such as, for example, breast cancer, colon cancer, prostate cancer, autoimmune diseases, e.g. systemic Lupus erythematosus, schizophrenia, depression, IgA nephropathy, sepsis and toxic shock, organ failure, organ transplants, coronary angioplasty, risk reduction for Alzheimer's disease, cystic fibrosis, atherosclerosis, menstrual discomfort, cyclic breast pain, premature labor, gout, venous leg ulcers, chronic urticaria, primary dysmenorrhea, endometriosis, and Lyme disease.

The compositions disclosed herein, including milk-based liquids having an unsaturated fatty acid portion, may contain from about 80–95% pure γ-linolenic acid, eicosapentaenoic acid, and stearidonic acid. These unsaturated fatty acids may be isolated from natural sources such as plants or animal tissues, or they may be isolated from transgenic cells engineered to produce at least one of the unsaturated fatty acids. Transgenic cells are defined as cells that include at least one stable heterologous gene, that, in this case are involved in producing the desired polyunsaturated fatty acid. Such genes may encode enzymes involved in a pathway that converts a precursor into the desired product, or that produce a precursor of the desired product, for example. Transgenic cells may include animal cells, yeast cells, plant cells, bacterial cells, or cyanobacterial cells, for example. It is also understood that such cells may be contained in an organism such as an animal, a plant, or a plant organ.

In certain embodiments, the present disclosure provides a method of inhibiting increases in serum arachidonic acid in a mammal to which γ-linolenic acid (GLA) has been provided, comprising providing to the mammal a $\Delta^5$ desaturase inhibitor. In particular aspects, the mammal has an inflammatory disorder. In particularly preferred embodiments, the $\Delta^5$ desaturase inhibitor is eicosapentaenoic acid (EPA).

Other $\Delta^5$ desaturase inhibitors contemplated to be useful in the present invention include sesamin, episesamin, sesaminol, sesamolin, curcumin, heneicosapentaenoic acid, alkyl gallate, propyl gallate, p-isopentoxyaniline, and docosahexaenoic acid. In such embodiments, an ω-3 competitive inhibitor of inflammatory cell AA metabolism and liver $\Delta^5$ desaturase activity may also be provided. Preferred examples are stearidonic acid and ω-3 arachidonic acid.

The GLA, EPA, and SA may be administered as free fatty acids or as fatty acyl esters. In particular aspects, the acyl esters may be triglycerides, ethyl esters, phospholipids, steryl esters or sphingolipids. The GLA, EPA, and SA may be administered in a single pharmaceutical or nutritional composition or as distinct pharmaceutical compositions or nutritional supplements. Preferred compositions are contained in a good tasting, milk based or juice based drink.

Particular aspects of the present invention provide a method of treating an inflammatory disorder in a mammal comprising providing to the mammal a γ-linolenic acid in an amount effective to increase the amount of dihomo-γ-linolenic acid (DGLA) in inflammatory cells and the circulation of the mammal; a $\Delta^5$ desaturase inhibitor in an amount effective to inhibit the formation of arachidonic acid in the serum of the mammal; and an amount of stearidonic acid effective to inhibit arachidonic acid metabolism in immune cells; wherein the increase in DGLA in the inflammatory cells of the mammal inhibits the metabolism of arachidonic acid and decreases the inflammatory response in the mammal. The inflammatory diseases may include, for example, asthma, allergic rhinitis, allergic rhinoconjunctivitis, arthritis, psoriasis, acute myocardial infarction, glomerulonephritis, Crohn's disease, inflammatory bowel disease, or any disease that is mediated by lipid inflammatory mediators as described herein.

Also contemplated herein is a dietary supplement preparation consisting essentially of GLA in an amount effective to increase the DGLA level in the user, such that the DGLA inhibits the metabolism of arachidonic acid in the inflammatory cells, and an amount of EPA which is effective to inhibit accumulation of arachidonic acid in the serum of the user. The dietary supplement of the invention is readily adapted for administration in unit dosage form for convenient delivery of a daily dose that consists essentially of GLA, present in an amount of from at least about 1 gram to about 15 grams, preferably about 1 gram to about 10 grams and most preferably about 1.5 to about 3 grams; EPA, present in an amount from about 0.1 grams to about 10 grams, preferably about 0.25 grams to about 5 grams and most preferably about 0.5 grams to about 3 grams; and, optionally, stearidonic acid (SA), present in an amount from about 0.1 gram, or even 1 gram to about 15 grams, preferably about 2 grams to about 10 grams and most preferably from about 3 grams to about 5 grams. When operating below the ranges specified the desired effects on eicosanoid synthesis and prevention of arachidonate accumulation will not be obtained. Operating above the indicated ranges will result in the consumption of large quantities of oils and may result in undesirable effects due to the large caloric intake from these oils.

Other objects, features and advantages of the present invention will become apparent from the following detailed description. It should be understood, however, that, the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 16A. GLA supplementation in combination with EPA. FIG. 16B. Stearidonic Acid Supplementation.

Abbreviations

Figure 1:
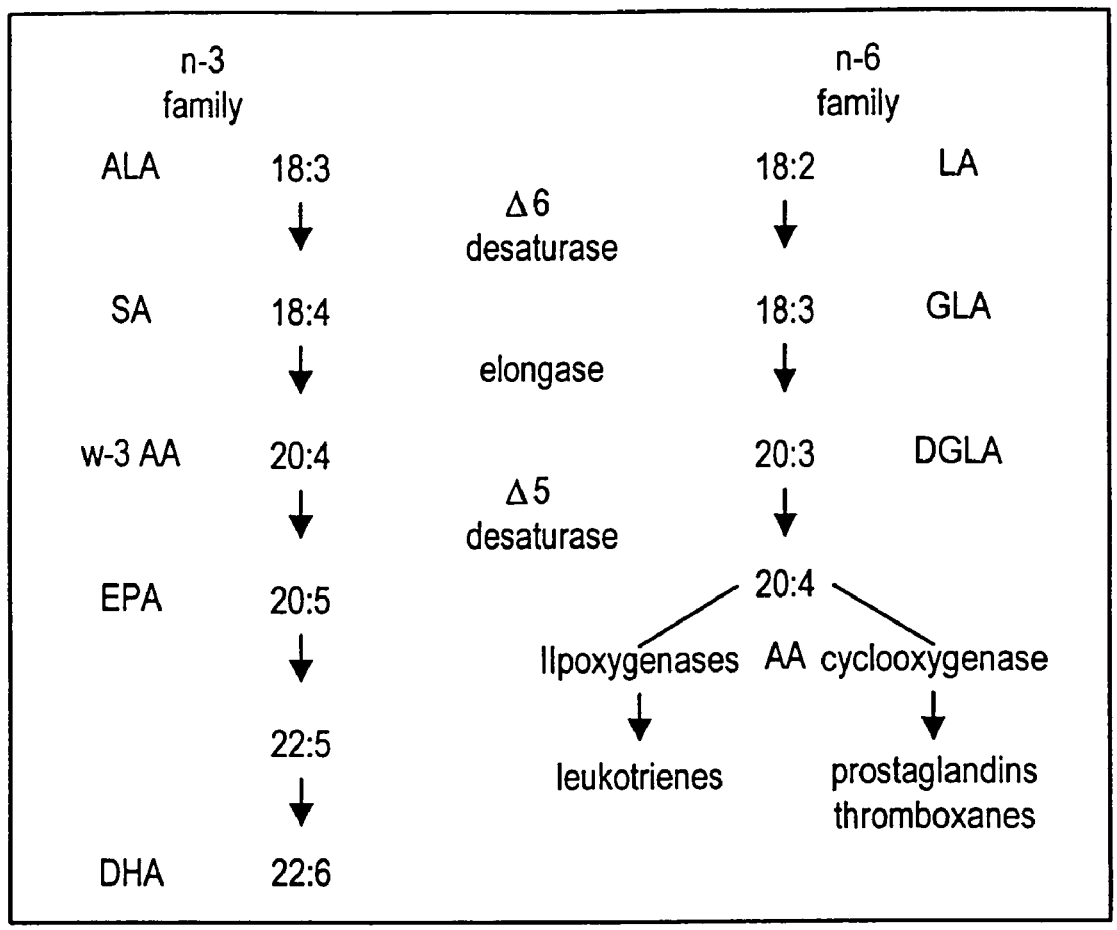
FIG. 1. Biochemical desaturation/elongation of essential fatty acids to polyunsaturated fatty acids.

AA, 20:4, arachidonic acid; EPA, 20:5 (n-3), eicosapentaenoic acid; LA, 18:2, linoleic acid; EFA, essential fatty acid; PUFA, polyunsaturated fatty acid; GLA, 18:3 (n-6), gammalinolenic acid; DGLA, 20:3 (n-6), dihomogammalinolenic acid; SDA, 18:4 (n-3), stearidonic acid; ω-3 AA, 20:4 (n-3); PC, phosphatidylcholine; PE phosphatidylethanolamine; PL phosphatidylinositol; GPC, sn-glycero-3-phosphocholine; GCRC, General Clinical Research Center; GC/MS, gas chromatography/mass spectrometry; NICI negative ion chemical ionization; TNF, tumor necrosis factor; FMLP, n-formyl-methionine-leucine-phenylalanine; TLC, thin layer chromatography; HPLC high pressure liquid chromatography; LTB$_4$, leukotriene B$_4$; LTB$_5$, leukotriene B$_5$; LTC$_4$ leukotriene C$_4$; PAF, platelet activating factor; HBSS, Hank's Balanced Salt Solution; BALF, bronchoalveolar lavage fluid; EAR, early asthmatic response; LAR, late asthmatic response.

DESCRIPTION OF ILLUSTRATIVE EMBODIMENTS

The present disclosure provides a dietary strategy, including nutritional supplements, designed to improve or at least partially alleviate symptoms of inflammatory disorders by providing a combination of polyunsaturated fatty acids, preferably in a milk or juice based, good tasting drink. The compositions and methods disclosed herein arose in part from the surprising discovery that human neutrophils lack a $\Delta^5$ desaturase activity, and that, while the use of γ-linolenic acid (GLA) in the treatment of arthritis or other inflammatory conditions leads to an increase in arachidonic acid (AA) in serum phospholipids, this increase does not occur in neutrophils. An alternate and synergistic method of inhibiting neutrophil AA metabolism and preventing serum accumulation of AA in response to increased GLA is also available in light of the present discovery. It was contemplated that stearidonic acid (18:4) would also be elongated in neutrophils to form ω-3 arachidonic acid, which would accumulate due to the lack of a $\Delta^5$ desaturase activity ($\Delta^5$ desaturase produces AA from ω-3 arachidonic acid). This excess of ω-3 arachidonic acid is available, then, to compete with natural AA (n-6) for enzymes (phospholipase A2 isotypes, cyclooxygenase isotypes, and 5-lipoxygenase) that convert AA to oxygenated metabolites. Concomitantly, ω-3 AA formed within the serum may be converted to eicosapentaenoic acid, possibly further inhibiting the hepatic $\Delta^5$ desaturase, and thereby contributing to the inhibition of accumulation of serum AA.

The present disclosure, thus, represents in part, a defined, three pronged mechanism of decreasing symptoms of inflammatory disorders. A precursor of arachidonic acid, such as GLA, may administered to a subject in order to reduce inflammation, as in conventional treatments. GLA administration to humans has been shown to effectively block AA metabolism, block the synthesis of AA products and mitigate the clinical symptoms of inflammatory disorders. As an additional element, the increase in arachidonic acid that is normally seen in serum fatty acids with administration of GLA may be inhibited by administering a $\Delta^5$ desaturase inhibitor, such as eicosapentaenoic acid (EPA), for example. This combination can be utilized in humans to inhibit $\Delta^5$ desaturation of DGLA to arachidonic acid in serum. Also disclosed herein is the synergistic step of providing for the synthesis of close structural analogs (antagonists) of AA by providing stearidonic acid, a competitive substrate of inflammatory cell elongase activity, which in this case, leads to ω-3 arachidonic acid. Thus, the antagonist of AA metabolism in the neutrophils and other inflammatory cells prevents the synthesis of the eicosanoids responsible for an inflammatory response without a concomitant increase in serum AA.

Figures 16A, 16B:
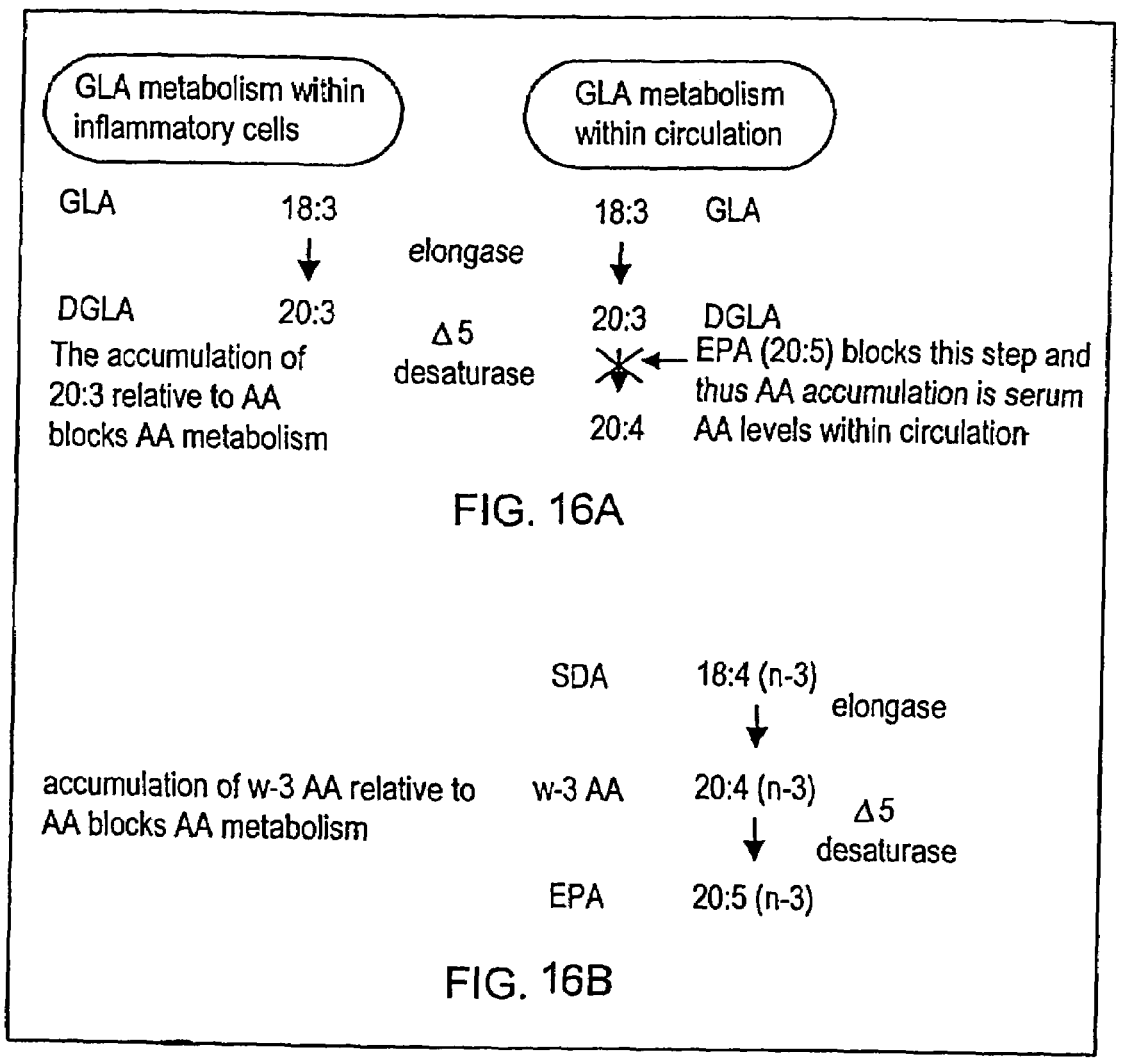
FIG. 16A and FIG. 16B. The two in vivo approaches to be used in order to synthesize close structural analogues of AA without affecting circulating AA levels.

The described strategy is based on the knowledge that when GLA is administered as a dietary supplement, an endogenous elongase activity in inflammatory cells synthesizes a close analogue of AA, DGLA (FIG. 16A). A part of the present disclosure is that certain inflammatory cells cannot further desaturate DGLA to AA because they lack a $\Delta^5$ desaturase. However, in human circulation, GLA becomes elongated to DGLA, and then is further desaturated to AA. This leads to a marked increase in AA level in the circulation as a result of GLA administration. The increased AA in the circulation has been shown to cause potentially detrimental effects such as increased platelet reactivity in humans (Seyberth et al., 1975).

The present invention includes a method of providing high concentrations of GLA to humans without causing a concomitant accumulation of serum AA. Thus, high concentrations of GLA can be administered to humans to synthesize DGLA in inflammatory cells, thereby inhibiting AA metabolism, eicosanoid synthesis and attenuating the signs and symptoms of inflammatory disorders without the significant side effect of circulatory AA accumulation. Specifically in the present invention, GLA is administered to humans in combination with $\Delta^5$ desaturase inhibitors including EPA. The present inventor has shown that this combination of GLA and the $\Delta^5$ desaturase inhibitor, EPA, causes a marked accumulation of DGLA in the circulation and in inflammatory cell lipids without causing an increase in accumulation of AA in serum lipids. Also described herein, the n-3 fatty acid, stearidonic acid (18:4) may be elongated in neutrophils to form ω-3 arachidonic acid (FIG. 1) resulting in a dose-dependent increase in ω-3 arachidonic acid in glycerolipids of these cells, and without an increase in the $\Delta^5$ desaturase product of ω-3 arachidonic acid, eicosapentaenoic acid, nor an increase in AA. Thus, high levels of the AA analog, ω-3 AA, can be induced in inflammatory cells by providing inflammatory cells (in vitro or in vivo) with stearidonic acid, which may be converted to ω-3 AA to compete with natural AA (n-6) for enzymes (phospholipase $A_2$ isotypes, cyclooxygenase isotypes, and 5-lipoxygenase) that convert AA to oxygenated metabolites.

Thus, the present invention provides combined compositions of GLA, EPA, and optionally SA, for example, for the treatment of inflammatory disorders such as psoriasis, rheumatoid arthritis, inflammatory bowel disease, Crohn's disease, ulcerative colitis, asthma, renal inflammation, atopic dermatitis, thyroiditis, or any other disease, syndrome, condition or disorder that is mediated by lipid inflammatory mediators. Included in the latter category are diseases such as breast cancer, colon cancer, prostate cancer, autoimmune diseases, e.g. systemic Lupus erythematosus, schizophrenia, depression, IgA nephropathy, sepsis and toxic shock, organ failure, organ transplants, coronary angioplasty, risk reduction for Alzheimer's disease, cystic fibrosis, atherosclerosis, menstrual discomfort, cyclic breast pain, premature labor, gout, venous leg ulcers, chronic urticaria, primary dysmenorrhea, endometriosis, and Lyme disease. To those skilled in the art it will be apparent that all of these conditions have an inflammatory component that includes a role for arachidonic acid metabolites.

The present invention provides methods and compositions for altering the serum arachidonic acid levels of a mammal in need of GLA supplementation by providing a $\Delta^5$ desaturase inhibitor in an amount effective to prevent or inhibit the accumulation of AA in the serum of said mammal. In preferred aspects, the present inventor has found that EPA is an in vivo and in vitro inhibitor of $\Delta^5$ desaturase activity in the liver of humans. Thus, administration of a combination of GLA and EPA will serve to prevent the synthesis of AA and its metabolites in neutrophils, whilst inhibiting the accumulation of AA in the serum. These methods and compositions are discussed in further detail herein below.

Sources of Fatty Acids for Use in Dietary Supplements

The fatty acyl compositions of the present invention may be obtained from a variety of sources. These acids may form part of a phospholipid, steryl ester, a sphingolipid, a glyceride, such as a di- or triglyceride or may be present as free fatty acids. For a comprehensive treatise of the synthesis of fatty acyl containing lipids, one of skill in the art is referred to "Lipid: Chemistry, Biochemistry and Nutrition" (Mead et al., *Lipid: Chemistry, Biochemistry and Nutrition*, Plenum Press, New York, 1986). More particularly, the distribution of fatty acids in tissue lipids is described in Chapter 5. Of particular relevance are chapters 11, 14, 15, 17, and 18 which describe synthesis and metabolic relevance of eicosanoids, triacylglycerols, steryl esters, phosphoglycerides and sphingolipids.

GLA may be obtained from sources such as oils of evening primrose, borage, blackcurrant, and various fungi and algae including Mucor, Rhizopus and Spirulina. DGLA may be synthesized from GLA or alternatively, may be obtained from a variety of animal tissues including, liver, kidneys, adrenals, or gonads. AA can also be isolated from similar tissues, or from egg yolk, and can also be found in various fungal and algal oils. EPA may be found in marine oils and various algal and fungal oils. Of course, although rather difficult and expensive, all the fatty acids may also be chemically synthesized de novo.

It is also an aspect of the present disclosure that, because specific, purified fatty acids are desired, certain organisms may be engineered to "overproduce" these particular fatty acids, making them easier to isolate and purify. For example, bacterial cells, cyanobacterial cells, fungal cells, yeast cells, plant cells, animal cells, or even organs, organelles or whole plants or animals may be engineered to overproduce or even to secrete the fatty acids needed for the compositions disclosed herein.

For example, gene sequences may be isolated that encode a single enzyme in the pathway leading to a fatty acid product, such as a $\Delta^6$ desaturase gene, for example, as described in U.S. Pat. No. 5,689,050, (incorporated herein by reference), for use in the practice of the present invention, or an entire pathway may be isolated from genomic clones, as described in U.S. Pat. No. 5,683,898 (incorporated herein by reference). In certain embodiments, an organism or a cell of an organism is selected that produces a precursor to a desired fatty acid, and in such cases, genes encoding the "downstream" enzyme or enzymes may be provided. It also understood that even if a cell produces the selected fatty acid, the production may be enhanced or increased by supplying additional copies under the control of more active promoter regions, or even inducible promoters so that expression of the genes may be controlled. Such systems are well known in the art.

The present invention may be described in terms of methods of treatment and pharmaceutical compositions, but it is understood that the GLA, EPA, SA and any other fatty acid used in the practice of the present invention may be incorporated into a dietary margarine, milkshake, a fraction of whole milk, a milk product, a juice, combination of juices or fruit product or other foodstuff. Pharmaceutical and dietary compositions comprising fatty acyl components are well known to those of skill in the art and have been described in U.S. Pat. Nos. 4,666,701; 4,576,758; 5,352,700; 5,328,691; 4,444,755; 4,386,072; 4,309,415; 4,888,326; 4,965,075, and 5,178,873; in European Patent Nos. EP 0 713 653, and EP 0 711 503; and in PCT Applications WO 96/31457 and WO 97/21434 (each of which is specifically incorporated herein by reference).

$\Delta^5$ Desaturase Inhibitors

As discussed earlier, AA and compounds derived therefrom are central mediators of inflammatory and allergic responses. A mechanism for ameliorating the deleterious effects of these compounds is through dietary control. One such manipulation involves the production or use of natural antagonists of AA at the sites of action of these compounds, inflammatory cells. Dietary supplementation with GLA has been shown to be effective at lowering inflammatory response, and it appears that although neutrophils (inflammatory response cells) take up GLA and elongate it to DGLA, there is no subsequent production of the eicosanoids that mediate inflammatory response. As shown herein, this effect occurs because neutrophils do not possess a $\Delta^5$ desaturase, thus the DGLA produced is not desaturated to AA. However, although neutrophils lack a $\Delta^5$ desaturase, other cells in the circulatory system do have $\Delta^5$ desaturation capabilities and such cells readily elongate the supplemented GLA to DGLA and desaturate that DGLA to AA. This increased circulatory AA is a potently harmful agent, and it is this problem that is addressed as an aspect of the present disclosure. Based on the discoveries disclosed herein, this potentially harmful accumulation of AA in the circulation of GLA-supplemented individuals can now be prevented by a concomitant provision of a $\Delta^5$ desaturase inhibitor.

EPA is an $\omega$-3, 20 carbon fatty acid that contains five double bonds (20:5), and as such is a structural analogue of AA (20:4). EPA has been shown to act as a $\Delta^5$ desaturase inhibitor, presumably via a feedback inhibition mechanism. Methods of producing this fatty acid have been well described in the art (e.g. U.S. Pat. Nos. 5,683,898; 5,567,732; 5,401,646; 5,246,842; 5,246,841; 5,215,630 each incorporated herein by reference). The present invention, in preferred embodiments, employs EPA as a $\Delta^5$ desaturase inhibitor to be administered in a nutritional supplement to those individuals receiving GLA supplements, in order to prevent the accumulation of AA in the circulation of said individuals.

In certain embodiments, it is contemplated that other inhibitors of $\Delta^5$ desaturase will also be useful, such compounds include members of the sesamin family, members of the curcumin family and other fatty acids such as docosahexaenoic acid, and heneicosapentaenoic acid. U.S. Pat. No. 5,674,853, which is specifically incorporated herein by reference, describes the use of lignins from the sesamin family in combination with saponin compositions as enteral formulations for treatment of infection and inflammation. Such sesamins will be useful in the context of $\Delta^5$ desaturase inhibition as described herein.

U.S. Pat. No. 5,336,496, incorporated herein by reference, describes other inhibitors of $\Delta^5$ desaturase that may be useful in the context of the present invention. In general terms, the $\Delta^5$ desaturase inhibitors described therein include lignan compounds, curcumin and piperonyl butoxide. As used herein the term "lignan" includes compounds such as sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane; 2,6-bis-(3-methoxy-4-hydroxyphenyl)-3,7-dioxabicyclo[3.3.0]octane; and 2-(3,4-methylenedioxyphenyl)-6-(3-methoxy-4-hydroxyphenoxy)-3,7-dioxabicyclo[3.3.0]-octane.

Methods of producing and separating these compounds are well known to those of skill in the art. For example U.S. Pat. No. 5,209,826 describes a method of separating sesamin and episesamin. It is contemplated that the present invention may use such methods in obtaining $\Delta^5$ desaturase inhibitors. As such, U.S. Pat. No. 5,209,826 is incorporated herein by reference. In other embodiments, the present invention employs microorganisms or plants, for example, for producing fatty acids as inhibitors of $\Delta^5$ desaturase. Such techniques are well known to those of skill in the art (e.g., Shimizu et al., 1988; Shimizu et al., 1989).

Methods for the synthesis of curcumin-related compounds have been described in U.S. Pat. No. 5,679,864 (incorporated herein by reference). These methods involve reacting the enol form of a 2,4-diketone with a monocarbocyclic aldehyde in the presence of an organic amine catalyst. The reactants are dissolved in a highly polar, aprotic, organic solvent. The curcumin-related product is recovered in crystalline form by precipitation from the reaction mass and solvent recrystallization and may be further purified using chromatographic techniques. The synthesis of naturally occurring curcuminoids and related compounds is well known in the art. The skilled artisan is referred to e.g., Pedersen, et al., *Ann. Chem.*, 1557–69, 1985; Arrieta et al., *J Prakt. Chem.*, 334:656–700, 1991 and Roughly et al., *JCS Perkins Trans I*, I, 2379–88, 1973, for guidance regarding detailed description of such synthesis and characterization.

Methods of Detection and Purification

The present invention concerns the provision, for example, as dietary supplements of a number of fatty acyl compositions. The fatty acid metabolism in circulatory and neutrophil cells has a balance of different precursors and substrates of arachidonic acid metabolism. In providing exogenous fatty acids as dietary supplementation, this baseline balance of fatty acids likely is altered. In certain instances it may be necessary to monitor the levels of the different fatty acids present in an individual's circulation and/or neutrophils. The present invention encompasses methods for the determination of the fatty acyl content of cells. These methods can also be employed for purifying fatty acids for inclusion as part of a dietary supplement. Generally, these methods will follow the methods described in the examples of the initial characterization of lipid content.

Chromatographic Methods of Detection

Briefly, one generally will isolate the lipid components of a cell as described herein. Separation of lipid components from (i) non-lipid components and (ii) each other will then permit quantitation of the different lipid species. Quantitation of separated components may be achieved by any standard methodology, that would include photodensitometric scanning of TLC plates or scintillation counting of membrane bound or liquid samples separated by various chromatographic techniques.

Any of a wide variety of chromatographic procedures may be employed. For example, thin layer chromatography, gas chromatography, high performance liquid chromatography, paper chromatography, affinity chromatography or supercritical flow chromatography may be employed. See Freifelder, *Physical Biochemistry Applications to Biochemistry and Molecular Biology*, $2^{nd}$ ed. Wm. Freeman and Co., New York, N.Y., 1982.

Partition chromatography is based on the theory that, if two phases are in contact with one another, and if one or both phases constitute a solute, the solute will distribute itself between the two phases. Usually, partition chromatography employs a column that is filled with a sorbent and a solvent. The solution containing the solute is layered on top of the column. The solvent is then passed through the column continuously, which permits movement of the solute through the column material. The solute can then be collected based on its movement rate. The two most common types of partition chromatography are paper chromatography and thin-layer chromatography (TLC); together these are called adsorption chromatography. In both cases, the matrix contains a bound liquid. Other examples of partition chromatography are gas-liquid and gel chromatography.

Paper chromatography is a variant of partition chromatography that is performed on cellulose columns in the form of a paper sheet. This technique may be useful in identifying and characterizing the lipid content of a particular sample. Cellulose contains a large amount of bound water even when extensively dried. Partitioning occurs between the bound water and the developing solvent. Frequently, the solvent used is water. Usually, very small volumes of the solution mixture to be separated are placed at the top of the paper and allowed to dry. Capillarity draws the solvent through the paper, dissolves the sample, and moves the components in the direction of flow. Paper chromatograms may be developed for either ascending or descending solvent flow. Two dimensional separations are permitted by changing the axis of migration 90° after the first run.

Thin layer chromatography (TLC) is very commonly used to separate lipids and, therefore, is considered a preferred embodiment of the present invention. TLC has the advantages of paper chromatography, but allows the use of any substance that can be finely divided and formed into a uniform layer. In TLC, the stationary phase is a layer of sorbent spread uniformly over the surface of a glass or plastic plate. The plates are usually made by forming a slurry of sorbent that is poured onto the surface of the gel after creating a well by placing tape at a selected height along the perimeter of the plate. After the sorbent dries, the tape is removed and the plate is treated just as paper in paper chromatography. The sample is applied and the plate is contacted with a solvent. Once the solvent has almost reached the end of the plate, the plate is removed and dried. Spots can then be identified by fluorescence, immunologic identification, counting of radioactivity, or by spraying varying reagents onto the surface to produce a color change.

In Gas-Liquid chromatography (GLC), the mobile phase is a gas and the stationary phase is a liquid adsorbed either to the inner surface of a tube or column or to a solid support. The liquid usually is applied as a solid dissolved in a volatile solvent such as ether. The sample, which may be any sample that can be volatized, is introduced as a liquid with an inert gas, such as helium, argon or nitrogen, and then heated. This gaseous mixture passes through the tubing. The vaporized compounds continually redistribute themselves between the gaseous mobile phase and the liquid stationary phase, according to their partition coefficients.

The advantage of GLC is in the separation of small molecules. Sensitivity and speed are quite good, with speeds that approach 1000 times that of standard liquid chromatography. By using a non-destructive detector, GLC can be used preparatively to purify grams quantities of material. The principal use of GLC has been in the separation of alcohols, esters, fatty acids and amines.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding, and it should be possible to elute the substance without destroying the sample or the ligand. One of the most common forms of affinity chromatography is immunoaffinity chromatography. The generation of antibodies that would be suitable for use in accord with the present invention is discussed below.

Pharmaceutical Compositions and Routes of Administration

The nutritional compositions of the present invention will have an effective amount of a $\Delta^5$ desaturase inhibitor, optionally an $\omega$-3 competitive inhibitor of AA metabolism such as stearidonic acid, and GLA, alone or in combination with other dietary supplements. Such compositions will generally be dissolved or dispersed in an acceptable carrier or medium, preferably for oral or topical administration. In certain embodiments, the compositions may be formulated for intravenous, intraarterial, intramuscular, nasal, vaginal, or anal administration, however, in certain embodiments the preferred medium is a milk-based or juice based liquid.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredients, its use in the therapeutic compositions is contemplated. Supplementary active ingredients, such as other fatty acid supplements, vitamins, minerals, non-steroidal anti-inflammatories, etc. can also be incorporated into the compositions.

The compounds are generally formulated for oral administration. Such pharmaceutically acceptable forms include, e.g., capsules, particularly gel capsules, or any other form currently used, including cremes, and liquids, for example syrups, suspensions or emulsions, inhalants and the like.

A liquid formulation will generally consist of a dispersion of the fatty acid compositions in a suitable liquid carrier(s) for example, water and/or other solvents such as, for example, polyethylene glycols, oils, milk, phospholipids, with, in certain formulations, a suspending agent, emulsifier, preservative, anti-oxidant, flavoring, and/or coloring agents. Preferred ingredients may include any of the following: galactolipids, sphingolipids, lecithins, cellulose, malt or malt extract, gelatin, casein, cholesterol, egg yolk, sodium dodecyl sulfate, benzalkonium chloride, p-hydroxybenzoic acid, vitamin C, vitamin E or alpha-tocopherol. A composition in the form of a dried powder may be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, a dispersion or suspension can be prepared using any suitable pharmaceutical carrier(s), for example aqueous gums, celluloses, silicates or oils and the dispersion or suspension then filled into a soft gelatin capsule.

Preferably the composition is in unit dose form such as a tablet, capsule, canned drink, or powder. Each dosage unit for oral administration contains preferably from about 1 to about 15 g of GLA and between about 0.1 and 10 g of EPA or a pharmaceutically acceptable salt thereof calculated as the free base.

The pharmaceutically acceptable compounds of the invention will normally be administered to a subject in a daily dosage regimen. For an adult patient this may be, for example, an oral dose of GLA between 1 gram and 15 grams, preferably between 1 gram and 10 grams, and most preferably between 1.5 grams and 3 grams, an oral dose of EPA between 0.1 g and 10 grams, preferably between 0.25 grams and 5 grams and most preferably between 0.5 grams and 3 grams, and optionally an oral dose of SA between about 0.1 g and about 15 g. The pharmaceutical compositions may be administered 1 to 4 times per day. Thus in particular embodiments, compositions are contemplated comprising a 1:1 (w/w) ratio of GLA: EPA, wherein there may be 1, 2, 3, 4, 5, 6, 7, 8, 9, or 10 grams of GLA. In other embodiments there may be a 2:1 ratio of (w/w) ratio of GLA:EPA, wherein there may be 1, 2, 3, 4, 5, 6, 7, 8, 9, 10, 11, 12, 13 14 or 15 grams of GLA. Of course, the ratio of GLA:EPA administered may be varied from that disclosed herein above, however, it is desirable to include the lowest effective amount of EPA or other fish-derived oils because of undesirable odors and flavors associated with those oils. For example, any amount of EPA including 0.1, 0.25, 0.5, 1, 2, 3, 4, 5, 6, 7, 8, 9 or 10 grams of EPA may be administered with any amount of GLA including 1, 2, 3, 4, 5, 6, 7, 8, 9, 10, 11, 12, 13, 14, or 15 grams of GLA. Such amounts of either supplement may be admixed in one composition or may be in distinct compositions.

The preparation of a composition that contains the $\Delta^5$ desaturase inhibitor (EPA), stearidonic acid, and GLA compounds alone or in combination with other supplements as active ingredients will be known to those of skill in the art in light of the present disclosure. Typically, such compositions can be prepared as liquids for capsules; solid forms or suspensions; the preparations can also be emulsified.

The dietary supplement comprising the combined $\Delta^5$ desaturase inhibitor and GLA formulations of the present invention may be in the form of ingestible liquids. For example, European patent application number EP 0713 653 A1 and EP 0711 503 A2 (incorporated herein by reference) describe fruit juices and milk based liquids that can be fortified with GLA and other dietary supplements. In alternative embodiments, the combined $\Delta^5$ desaturase inhibitor and GLA formulations of the present invention may be incorporated into a dietary margarine or other foodstuff.

Solutions of the active compounds as free base or pharmacologically acceptable salts can be prepared in liquid suitably mixed with a surfactant, such as hydroxypropylcellulose. Dispersions can also be prepared in glycerol, liquid polyethylene glycols, and mixtures thereof, and in oils. Under ordinary conditions of storage and use, these preparations contain a preservative to prevent the growth of microorganisms.

The pharmaceutical formulations suitable for ingestion may include sesame oil, evening primrose oil, peanut oil, aqueous propylene glycol, and sterile powders. In all cases it is desirable to keep the formulation sterile and stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts and those which are formed with inorganic acids such as, for example, hydrochloric or phosphoric acids, or such organic acids as acetic, oxalic, tartaric, mandelic, and the like. Salts can also be derived from inorganic bases such as, for example, sodium, potassium, ammonium, calcium, or ferric hydroxides, and such organic bases as isopropylamine, trimethylamine, histidine, Procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the compositions can be brought about by the use in the compositions of agents delaying absorption, for example, aluminum monostearate and gelatin.

Sterile compositions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders, the preferred methods of preparation are vacuum-drying and freeze-drying techniques which yield a powder of the active ingredient.

Upon formulation, the active ingredients will be administered in a manner compatible with the dosage formulation and in such amount as is therapeutically effective. The formulations are easily administered in a variety of dosage forms, such as tablets containing measured amounts of active ingredient, with even drug release capsules and the like being employable. The amounts of active ingredients in the formulations of the present invention will be similar to fatty acid supplements currently available. Those of skill in the art are referred to the Physicians Desk Reference for more comprehensive details on currently used dosages of food supplements. Some variation in dosage will necessarily occur depending on the condition of the subject being treated. The person responsible for administration will, in any event, determine the appropriate dose for the individual subject.

For dietary or nutriceutical use, an inhibitor of $\Delta^5$ desaturase, alone or in combination with other dietary supplements may be formulated into a single or separate pharmaceutically acceptable compositions. Preferably formulations include a good tasting, milk based drink, or a good tasting, juice based drink or fruit based powder. Such a drink may be contained in cans, preferably cans sealed under nitrogen or other oxidatively inert gas atmosphere. Cans may be packaged in "six packs" held together by plastic or cardboard containers for easy retail sales. The drinks may also be enclosed in individual cardboard or aluminum based or other foil containers, for example, that also provide a straw for each individual container. The drink formulations may also be provided in dried or lyophilized forms for rehydration in milk, water, juice, or other suitable solvent. In certain embodiments, a pre-measured liquid container indicating the level of liquid needed for proper rehydration may be included, and in bulk powder containers, a measuring spoon may also be provided. It is also understood that individual packets may be provided that each include enough powder for a single serving.

The following described materials and methods were used in the studies described in the Examples, below, unless otherwise indicated.

Cell and Serum Preparations

Neutrophils are obtained from venous blood of healthy human donors as described (Lykens et al., *Am. J. Physiol, Lung Cell Mol. Physiol.*, 262:L169–L175, 1992).

Eosinophils are purified by negative, immunomagnetic selection using monoclonals against FcKRIII (CD 16) present on neutrophils. Antibody tagged neutrophils are then incubated with anti-mouse IgG conjugated magnetic beads and removed by filtration over a magnetized steel wool column.

Monocytes are obtained as follows: a mononuclear cell layer is obtained from normal human blood after centrifugation over isolymph and washed in HBSS without $Ca^{2+}$ or $Mg^{2+}$, with 0.1% gelatin and 2 mM glucose, pH 7.4. Mononuclear cells are further separated by centrifugation over discontinuous Percoll gradients (45°/50.5%, 15 min, 300×g) to obtain a rough separation of monocytes from lymphocytes, washing, and then centrifugation over 48% Percoll (15 min, 300×g) to remove contaminating lymphocytes.

In order to obtain Alveolar Macrophage (AM), BAL fluid samples are strained through a monolayer of coarse mesh surgical gauze and total cell counts and differentials determined. Cells are pelleted, resuspended in PBS, and washed 3 times. In normal individuals, ~1 to $1.5 \times 10^7$ total cells are expected with ~85% of harvested cells being AM. When necessary (to attain a population of at least 85% AM), AM are further purified by centrifugation (300×g, 15 min) over 48% Percoll. Cells are washed (3× in buffer and resuspended at $1 \times 10^7$ cells/ml in HBSS.

Serum is extracted from 2 ml of venous blood from donors. Briefly, blood samples are incubated at 37° C. for 30 min. Blood clots are removed from the serum by centrifugation (600×g, 10 min). Residual red blood cells are removed from the serum by centrifugation using a Beckman Microfuge E for 5 min. After the addition of 1.9 ml of water to a 0.1 ml aliquot of the serum, lipids are extracted by the method of Bligh and Dyer (Bligh and Dyer, *Can. J. Biochem. Physiol.*, 37:911–920, 1959); Chilton et al., *J. Biol. Chem.*, 258:7268–7271, 1983). A portion (5%) of the extracted lipids is used to determine the mole quantities of fatty acids by GC/MS. Serum components are isolated into individual glycerolipid classes by TLC (System II or normal phase HPLC (Bligh and Dyer, 1959).

Chromatography Techniques

Phospholipid classes (PE, PS, PL and PC) are separated by normal phase HPLC using an Ultrasphere-Si column (4.6×250 mm) eluted initially with hexane:2-propanol:ethanol:25 mM phosphate buffer (pH 7.4):acetic acid (490:367: 100:30:0.6, v/v) at a flow rate of 1 ml/min. After 5 min, the composition of the phosphate buffer is increased to 5% over a 10 min period to elute all phospholipids.

TLC of phospholipid subclasses. Phospholipid subclasses (diacyl-, alkylacyl-, alky-1-enylacyl-) are separated as diglyceride acetates or benzoates on silica gel G plates developed in benzene/hexane/ether (50:45:4, v/v). Briefly, the phosphobase moiety of phospholipids is removed by phospholipase C hydrolysis followed by the addition of acetic anhydride/pyridine (5:1, v/v).

Leukotrienes are separated by reverse phase HPLC utilizing an Ultrasphere ODS column (2.1 mm.×250 mm: Rainin Instrument Co, Woburn, Mass.) eluted with methanol/water/phosphoric acid (550:450:0.2 v/v, pH 5.7) as the mobile phase at 0.3 ml/min. After 5 min the methanol composition of the mobile phase is increased from 55% to 100% over a 20 min period. The mole quantities of each leukotriene are determined by examining its UV optical density at 270 nm. Individual peaks are integrated and their recoveries normalized by comparing these integrated areas to that of $PGB_2$ added as an internal standard.

GC/MS Analysis of Fatty Acids and Lipid Mediators

Free fatty acids are obtained from glycerolipids by base hydrolysis using 2 N KOH (30 min, 60° C.). After the addition of an equal volume of water, the pH of the reaction mixture is adjusted to 3 using 6 N HCl. Free fatty acids are then extracted with ethyl ether and converted to pentafluorobenzylesters using an equal volume of 20% pentafluorobenzylchloride in acetonitrile and 20% diisopropylethylamine in acetonitrile. The carboxylate anion of all fatty acids of interest and $[^2H_3]$-stearic acid and $[^2H_8]$-arachidonate (internal standard) are analyzed by NICI GC/MS using a Hewlett Packard mass spectrometer (HP 5989A).

Eicosanoids from ethyl acetate extracts of supernatant fluids are converted to methoxime-pentafluorobenzyl ester trimethylsilyl derivatives. These derivatives of $LTB_4$, $LTB_5$, $^2H_4$-$LTB_4$, $PGE_2$, $PGE_1$, $^2H_4$ $PGE_2$ and $^2H_4$ $PGE_1$ (internal standard) are analyzed on an HP selective mass detection system (Hewlett Packard 5989A) by selected ion monitoring techniques to record carboxylate anions at m/z 479, 477, 483, 524, 526, 528 and 530, respectively.

Urinary $LTE_4$

Aliquots of urine are spiked with $^3H$-$LTE_4$ and stored at −70° C. Urinary $LTE_4$ is then measured using the methods of Manning et al., *J. Allergy Clin. Immun.*, 86:211–220, 1990 utilizing reverse phase HPLC followed by RIA: (Christie, *J. Lipid Res.*, 26:607–612, 1985). Recovery is determined using the added $[^3H]$-$LTE_4$ as an internal standard. $LTE_4$ levels are expressed relative to urinary creatinine.

Subjects and Controlled Diets

Subjects are recruited by poster advertisements from the Medical Center staff and students. Inclusion criteria require healthy, normal men and women of all races, 21 to 55 years old; subjects who consume an omnivorous, nutritionally adequate diet consisting of at least 25% of calories from fat. Volunteers who are within 10% of ideal body weight (IBW) and do not exceed 30% and 35% body fat for men and women, respectively (as determined by anthrometric measurements in the GCRC). Diet compositions are determined by the food frequency questionnaire component of the Health Habits and History Questionnaire developed by the NCI (Shin et al., *Am. J. Respir. Crit. Care Med.*, 149: 660–666, 1994; Wenzel et al., *Am J. Respir. Crit. Care Med.*, 156:737–743, 1997).

Exclusion criteria include persons with any chronic or acute disease as determined by self report or physical screening; who are vegetarians or vegans; who are lactose or egg intolerant; who use drugs that affect AA release and subsequent metabolism (steroidal and non-steroidal anti-inflammatories); with serum cholesterol levels above 220 mg/cd; who are unable or unwilling to strictly adhere to a precise, restricted diet; who are unwilling to be randomly assigned to the diet group for whatever protocol the subject volunteers; who are smokers.

Composition of the diets are based on the USDA Handbook 8 and The Nutrition Data System from The Nutritional Coordinating Center of the University of Minnesota. For each of the protocols outlined above, the menus are designed with adjustments for each subject's energy needs. Basal energy expenditure is determined by the Harris-Benedict Equations:

Basal energy expenditure (BEE) for men=65+(13.7× Wt(kg))+(5×Ht(cm))–(6.8×age(yr))

for women=655+(9.6×Wt(kg))+(1.8×Ht(cm))–(4.7× age(yr)).

Total daily energy needs equal the BEE times an activity factor of from 1.3 for ambulatory but sedentary to 1.5 for the more active persons. Body weight is monitored each day when the subjects come to the Center to receive their meals. Calorie levels are adjusted appropriately.

Procedures and Specimens Collection Used in Human Model of a Topic Asthma

Clinical data on each patient is entered into a database consisting of the following elements. Demographic data (age, sex, race, smoking history), and the data elements used to fulfill the above diagnostic criteria, spirometric data, presence of atopy (positive "prick" skin testing to respirable antigens), presence of LAR to inhaled antigen, and presence of allergic rhinoconjunctivitis.

Allergen skin testing—Atopic asthmatic subjects are identified by skin testing using the skin prick method at a 1:10 (wt/vol) dilution of 20 stock antigen solutions (Greer Laboratories, Lenoir, N.C.). Subjects must not be receiving immunotherapy, nor may they be treated with systemic corticosteroids for a minimum of 4 wk. Short acting antihistamines are avoided for at least 24 h and long acting for at least 7 days. Atopic subjects are defined as those with a positive response consisting of a wheal of at least 3 by 3 mm to one or more antigens, with an appropriately negative saline control.

Allergen Inhalation Challenge—The immediate (early) asthmatic response (EAR) or late asthmatic response (LAR) is studied under controlled conditions using inhaled antigenic challenge in volunteer patients with asthma using a previously described protocol (Smith et al., *Clin. Pharm. Ther.*, 54:430–436, 1993). Atopic asthmatics undergo inhaled allergen challenge followed by BAL according to the following protocol. Subjects must have no lung disease other than asthma, and, on the day of testing, must have a baseline $FEV_1$>70% of predicted. Subjects must not be receiving immunotherapy, nor may they be treated with cromolyn sodium or corticosteroids (inhaled or systemic) or leukotriene antagonist for a minimum of 4 wk. Short-acting antihistamines are avoided for at least 24 h and intermediate acting for 7 days (astemizole for 6 weeks). Theophylline preparations are withheld for 24 h prior to challenge and beta-agonists for 8 h prior to challenge. On the day of challenge, subjects must be wheeze-free, with an $FEV_1$>than 80% of the previously observed highest value. If the patient has an intercurrent respiratory infection, inhalation challenge is postponed for at least 6 wk. Antigens to which the subject is perennially exposed (e.g., mite, cat) are utilized whenever possible to minimize the impact of seasonal variations in environmental exposure to the specific antigen. Further, antigen testing is conducted out of the respective allergen season, or after attempts to minimize environmental exposure (e.g., to mites or cats) have been implemented. Antigenic challenge generally begins between 7:30 and 8:00 am and the patient is monitored for a minimum of 12 h following antigenic challenge. Subjects inhale allergen to which they have previously demonstrated skin sensitivity beginning at 1:1,000,000 dilution (wt/vol) and proceeding with logarithmically increasing concentrations to 1:100. The subject breathes quietly from a continuous hand-held nebulizer for 2 min at each concentration. Following each concentration, the $FEV_1$ is measured at 5 min intervals (DS Plus, Warren E. Collins, Inc., Braintree, Mass.). If the $FEV_1$ does not fall by 20% after 15 min, the next higher concentration is administered. Once a 20% drop in $FEV_1$ is measured, or following the highest concentration, spirometry is performed every 15 min for the first hour and then hourly for the next 11 h. Patients experiencing symptomatic bronchospasm following initial antigenic inhalation may receive a short acting inhaled beta-agonist bronchodilator agent (isoproterenol). Thi S, has no effect on the subsequent late asthmatic response (LAR). An LAR is defined as a 15% or greater fall in $FEV_1$ from the prechallenge baseline value occurring between 3 to 12 h after challenge.

Bronchoalveolar lavage—Subjects whose $FEV_1$ immediately preceding bronchoscopy is less than 60% of prechallenge baseline do not undergo BAL to minimize further acute diminution of lung function and to maximize subject safety. Fiberoptic bronchoscopy is performed following methodologies previously detailed in the literature (Wenzel et al., *J. Allergy Clin. Immunol.*, 87:540–548, 1991; Zehr et al., *Chest*, 95:1059–1063, 1989). Briefly, the fiberoptic bronchoscope is introduced into the lower airways trans-nasally following nebulized 4% Xylocaine, topical anesthesia and benzodiazepine sedation, titrated to patient comfort Isoproterenol, 1 puff, 130 µg is administered 10 min before bronchoscopy. Bronchoalveolar lavage (BAL) is obtained from the right middle lobe or lingula utilizing six 50 ml aliquots (200 ml total volume) of sterile normal saline without preservatives, warmed to 37° C. The amount of BAL returned is recorded and the specimen promptly processed. The right middle lobe or lingula is routinely used to maximize the uniformity of specimen yield as the return from BAL is dependent upon many factors, but especially airway geometry and gravity. These areas tend to drain spontaneously by gravity in supine patients. This improves the return of fluid from the lavage as well as minimizing the amount of retained fluid within the lung in these patients.

BAL samples are strained through a monolayer of coarse-mesh surgical gauze and total cell yield determined by taking a small aliquot of the pooled, well mixed fluid, and counting the cells in a Neubauer hemocytometer. BAL cell count is expressed as the total number of cells recovered by lavage and as the number of cells per ml of recovered BAL fluid. A small aliquot is then cytocentrifuged (Shandon Southern Cytospin) for 5 min at 4,500 RPM, air dried, and stained by a modified Wright-Giemsa stain. A 300 cell differential count is performed where alveolar macrophages and other leukocytes are enumerated. The number of ciliated or squamous epithelial cells present are noted, but are not included in the differential count. Quantification of the cellular populations recovered by lavage are expressed as a percentage of the total cells recovered (excluding red blood cells and epithelial cells), and as the total numbers of each cell type recovered. The remaining BAL fluid is centrifuged at 500×g, 4° C., for 15 min. Aliquots of the supernate not immediately processed are stored at −80° C.

Effect of supplementation on eosinophil eicosanoid biosynthesis: 75 ml from a peripheral vein is collected 30 to 60 min prior to inhaled challenge and 24 h after challenge. Eosinophils are isolated as described above. Cells are challenged with A23187 (1 µM) and PAF (1 µM). Leukotrienes are quantified after reverse phase HPLC as described above. Quantities of free fatty acid and prostaglandins are determined by NICI GC/MS.

Urinary $LTE_4$: Urine is collected for 3 h beginning immediately after antigen challenge and again from 3 h until after the LAR. Urinary $LTE_4$ is measured using an RIA as described above.

Arachidonic acid release: Free fatty acid levels including AA in BAL are determined, after addition of $^2H_3$-stearidonic acid and $^2H_8$-AA to BAL as internal standards, by NICI-GC/MS.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE 1

In Vivo Studies Examining GLA Supplementation in Humans

Incorporation of Supplemented Fatty Acids into Serum Lipids

Initial studies examined the effect of dietary supplementation with GLA on the fatty acid content of serum lipids. Here, 9 healthy adult volunteers consumed a controlled eucaloric diet consisting of 25% fat, 55% carbohydrate and 20% protein prepared in the metabolic kitchen of the GCRC.

Four menus were served on a rotating basis throughout the study period. In addition, three groups of three volunteers supplemented this diet with three different doses of GLA.

Figure 2:
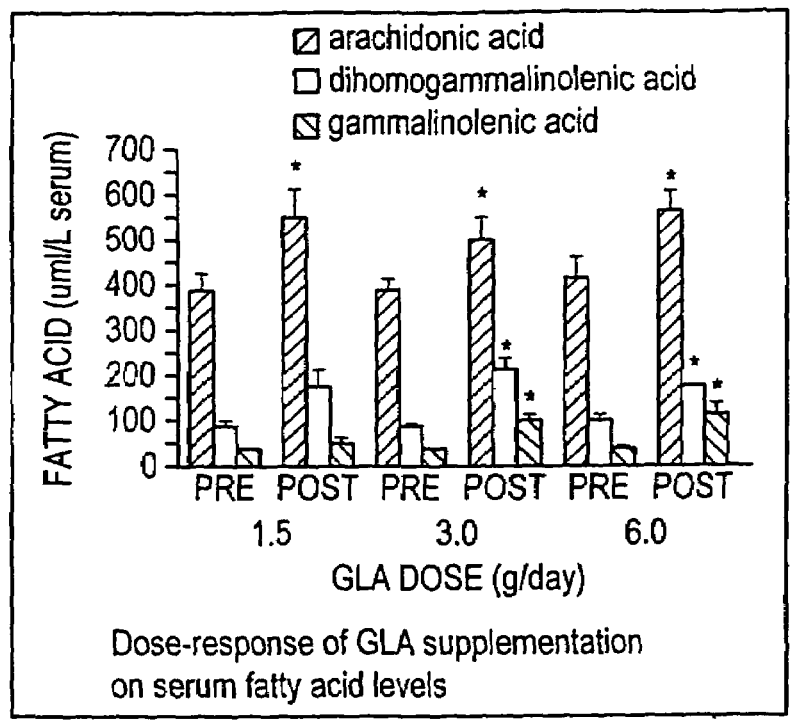
FIG. 2. Dose-response of GLA supplementation on serum fatty acid levels.

FIG. 2 demonstrates the effect of GLA supplementation at three different doses on serum levels of GLA, DGLA, and AA. In all three groups of subjects, AA significantly increased in serum lipids at the end of the three-week dietary period when compared with baseline values. Both GLA and DGLA significantly increased in the groups receiving 3.0 g/day and 6.0 g/day. In the two highest dose groups, DGLA levels increased two-fold and AA levels increased approximately 30% when compared to baseline values of these fatty acids in the same subjects. There was no significant change in serum fatty acid levels of volunteers eating control (25% energy as fat) diets, but not receiving the GLA supplement.

Figure 3:
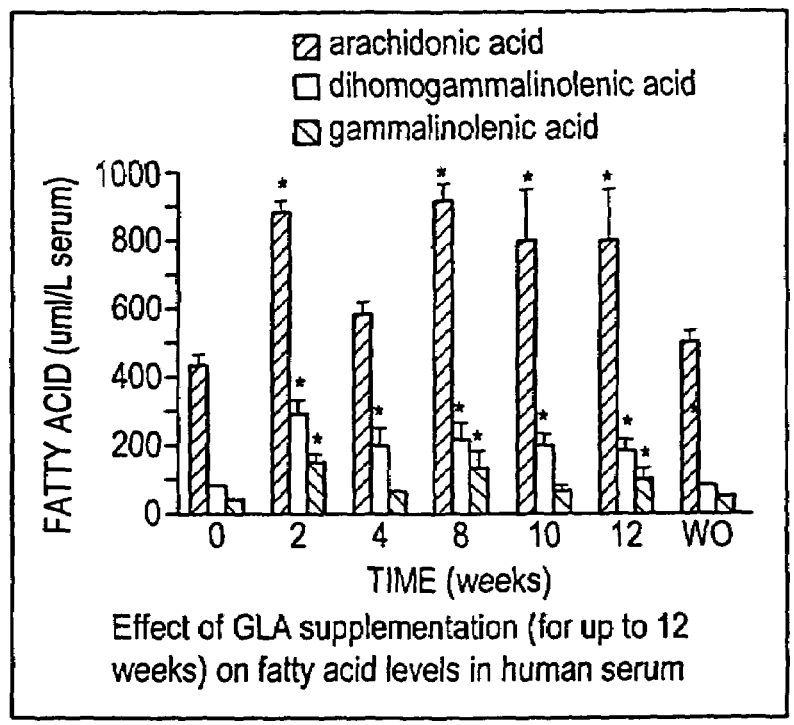
FIG. 3. Effect of GLA supplementation (up to 12 weeks) on fatty acid levels in human serum.

An important difference between the aforementioned studies and most clinical trials in the literature was the length of time of supplementation. Therefore, a long-term supplementation study (3.0 g/day) was performed over a 12-week period to assess whether fatty acid ratios and distribution would change in a manner that was not observed at three weeks. This study showed that there was a significant increase in serum GLA, DGLA, and AA levels by two weeks and that these levels stayed high over an additional 10 weeks of supplementation (FIG. 3). Taken together, these data suggest that although some dietary GLA remains in the serum unchanged, substantial quantities of the elongation product (DGLA) and the elongation/$\Delta^5$ desaturase product (AA), accumulate in serum after GLA supplementation.

The next set of studies was designed to determine the distribution of supplemented fatty acids or their metabolites within individual glycerolipid classes of serum. Serum was collected from volunteers before and after receiving 6.0 g/day of GLA. Serum glycerolipids were separated by TLC and fractions were analyzed for fatty acid content following base hydrolysis by NICI-GC/MS. GLA was located predominately in triglycerides (36–38% of total), phospholipids (26–33% of total), and cholesterol esters (17–21% of total). After supplementation, GLA significantly increased in both phospholipids and cholesterol esters. In contrast, DGLA and AA were almost exclusively located in serum phospholipids, with very little of these fatty acids found in other serum pools. After supplementation, both DGLA and AA increased only in phospholipid pools.

Incorporation of Supplemented Fatty Acids into Neutrophil Lipids

Figure 4:
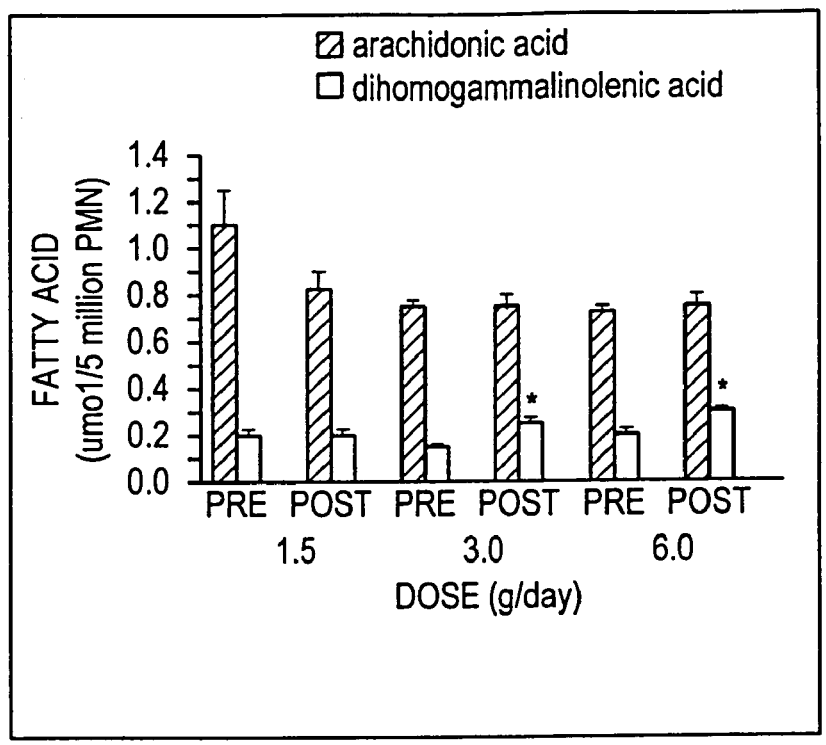
FIG. 4. Dose-response of GLA and metabolites supplementation into neutrophil lipids.

The fatty acid composition of the neutrophil lipids in subjects eating a controlled diet supplemented with 1.5, 3.0, or 6.0 g/day of GLA were also analyzed. No consistently detectable amounts of GLA were found in the glycerolipids of neutrophils before or after supplementation. Although relatively large quantities of AA were found in unsupplemented neutrophils, there was no significant change in AA within glycerolipids after supplementation at any of the doses given (FIG. 4). In contrast, DGLA within glycerolipids increased as a function of the dose provided to the volunteers. The AA/DGLA ratio decreased from approximately 5.4:1 before supplementation to 2.3:1 three weeks after 6.0 g/day of GLA supplementation. There was no significant change in fatty acid levels in control subjects eating the study diet without supplementation. These findings suggest that neutrophils rapidly elongate GLA to DGLA but lack the ability to desaturate DGLA to AA.

Figure 5:
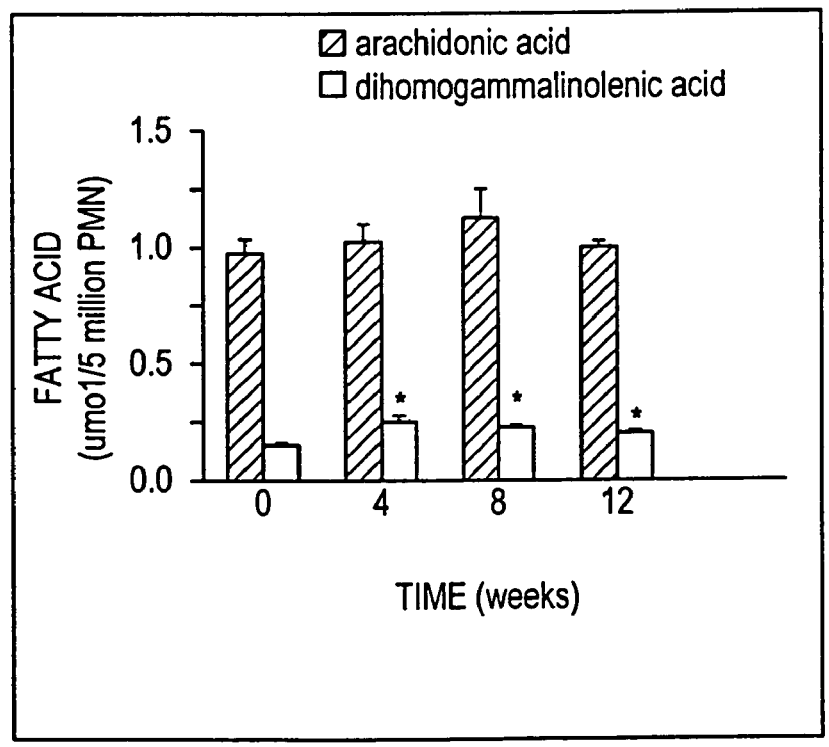
FIG. 5. Effect of GLA supplementation (up to 12 weeks) on fatty acid levels in human neutrophils.

The influence of long term (12 week) GLA supplementation (3 g/day) on the composition of GLA, DGLA and AA in neutrophil lipids also was examined. In contrast to serum, GLA supplementation resulted in an increase in DGLA but not AA even at 12 weeks (FIG. 5). It is not clear why the increase of AA in serum is not eventually observed in neutrophil lipids; perhaps this AA is in a serum pool not available to neutrophils. Taken together these preliminary data indicate that GLA provided as a dietary supplement is converted to different products (DGLA in inflammatory cells and AA in serum) depending on where it is metabolized. This results in the potentially beneficial effect of reducing AA metabolism in inflammatory cells balanced against the potential adverse effects of the accumulation of serum AA levels. These studies led to studies designed to determine whether it is possible to utilize the endogenous elongase activity within inflammatory cells to synthesize analogs of AA from appropriate dietary precursors without concomitantly increasing levels of circulating AA.

Figures 6A, 6B:
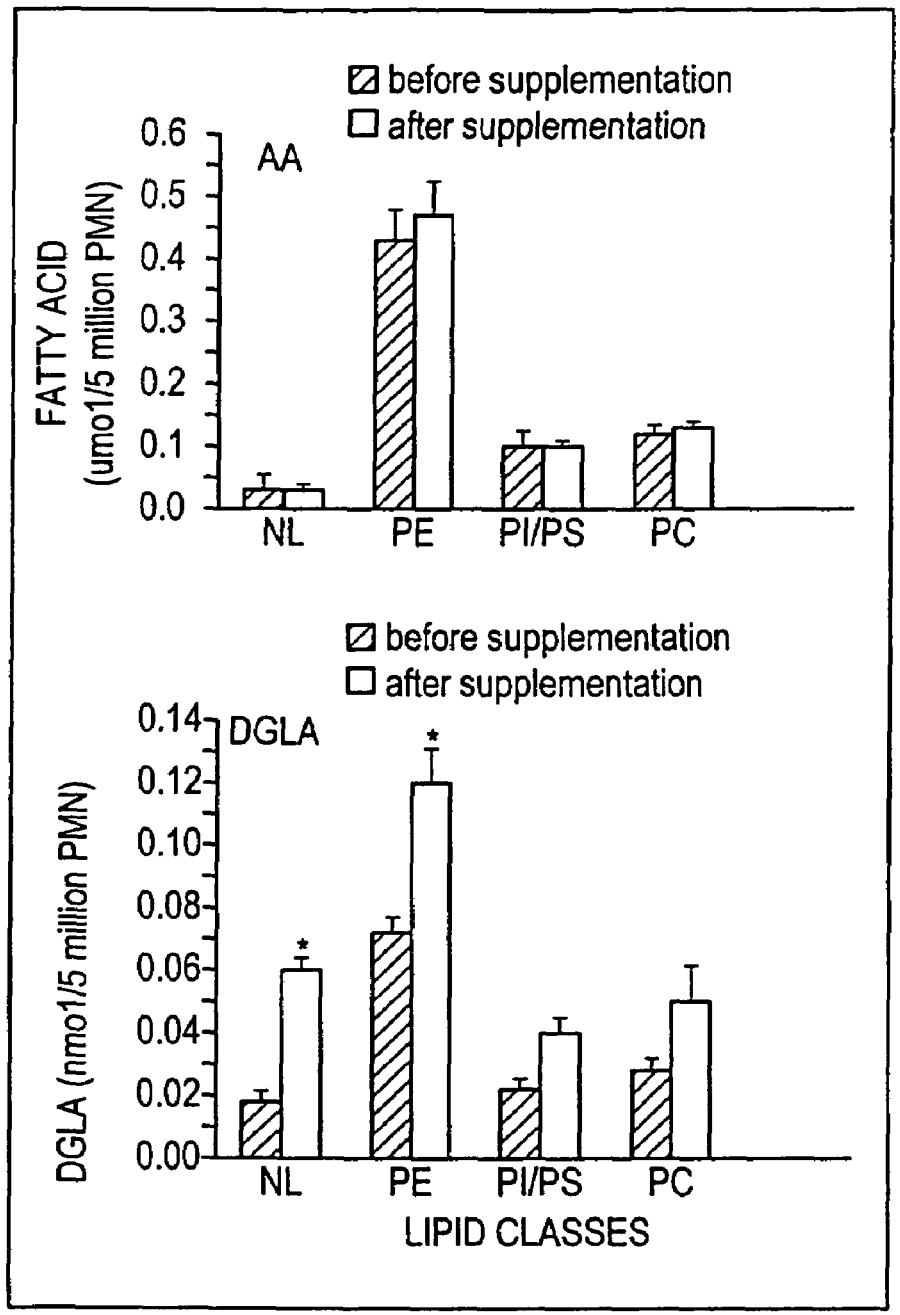
FIG. 6A and FIG. 6B. Incorporation of AA (FIG. 6A) and DGLA (FIG. 6B) into glycerolipid classes of neutrophils.

To better determine the distribution of fatty acids within different glycerolipid classes, neutrophils were obtained before and after supplementation with 6.0 g/day of GLA for 3 weeks and glycerolipids were separated by normal phase HPLC. Quantities of fatty acids in each glycerolipid class were then determined by NICI-GC/MS. As shown in FIG. 6A, the majority of AA (>60%) within the neutrophil lipids was located in phosphatidylethanolamine (PE) and neither the absolute amount nor its relative distribution changed significantly after dietary supplementation with GLA. Similarly, the bulk of DGLA in the neutrophil was associated with PE (40%) (FIG. 6B). There were significant increases in the amount of DGLA associated with both PE and neutral lipids after supplementation, For example, the AA/DGLA ratio in PE decreased from 8.3:1 before supplementation to 4:1 after supplementation. These data illustrate that AA and DGLA reside in similar glycerolipid pools both before and after supplementation.

Figure 7:
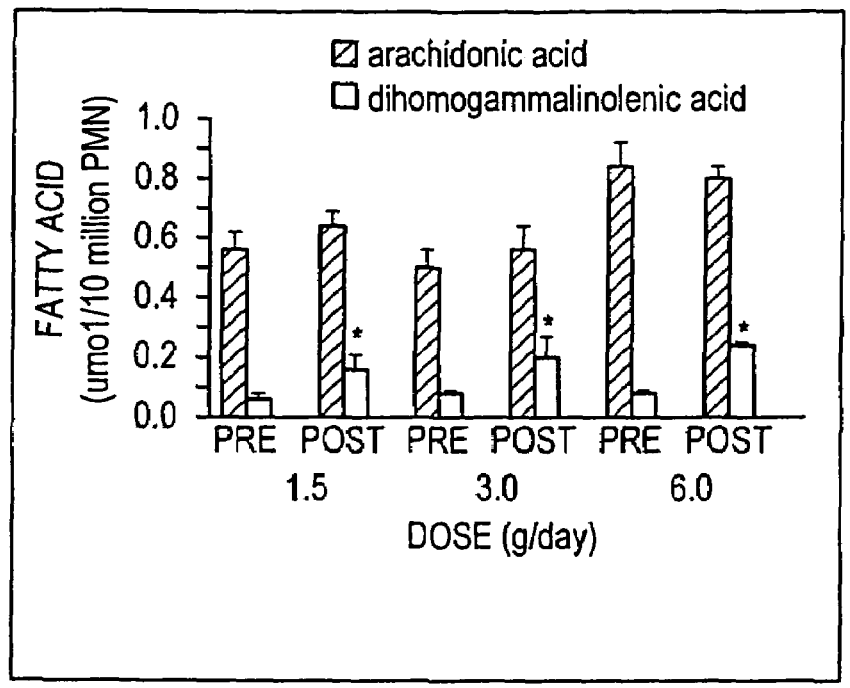
FIG. 7. Fatty acid release from stimulated neutrophils before and after supplementation.

Influence of GLA Supplementation on the Release of Fatty Acids or the Production of Lipid Mediators by Stimulated Neutrophils Neutrophils were next obtained from subjects before and after supplementation and stimulated with ionophore A23187. The release of AA from the neutrophil glycerolipids after stimulation did not change following supplementation. However, the release of DGLA increased by 63%, 65%, and 69% in those volunteers receiving 1.5 g, 3.0 g and 6.0 g/day GLA, respectively (FIG. 7). These data support the hypothesis that the fatty acid composition of the neutrophil glycerolipids impacts on the fatty acids released upon cellular stimulation. They also suggest that the $PLA_2$ isotype(s) enzyme responsible for mobilizing fatty acids hydrolyzes DGLA in addition to AA.

Figure 8:
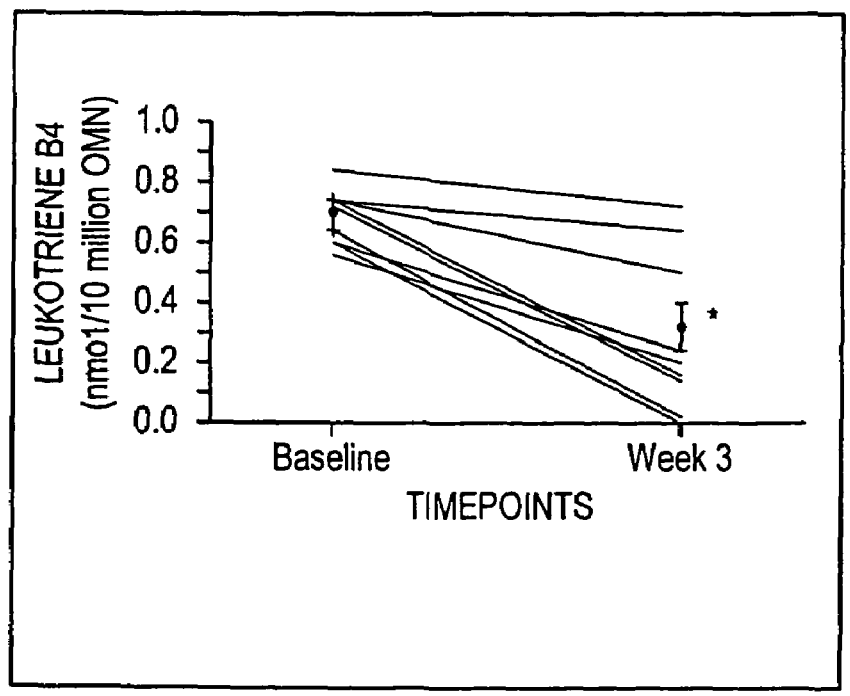
FIG. 8. Influence of GLA supplementation on leukotriene generation.
Figure 9:
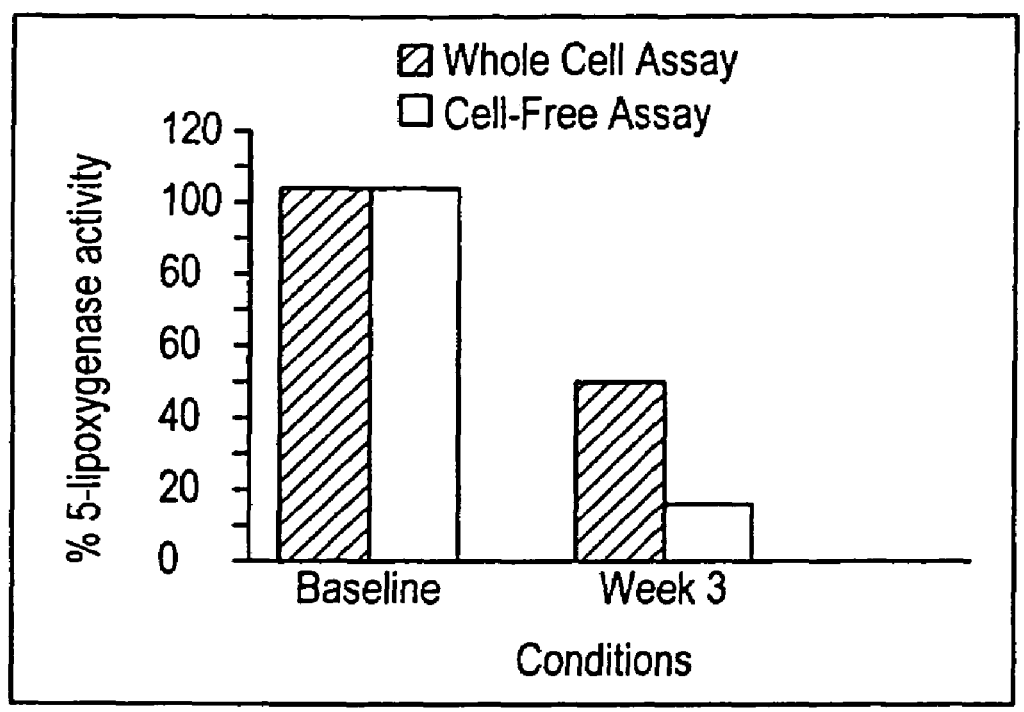
FIG. 9. Influence of GLA supplementation on 5-lipoxygenase activity.

While the aforementioned studies demonstrated that GLA supplementation did not influence the ex vivo release of AA from neutrophil glycerolipids, it was unclear whether GLA supplementation would alter leukotriene biosynthesis. To examine this question, neutrophils were stimulated and the synthesis of $LTB_4$, 20-OH $LTB_4$, and the 6 trans isomers of $LTB_4$ were measured by reverse phase HPLC analysis. Neutrophils from subjects supplementing their controlled diets with 3.0 g/day GLA produced 60% less $LTB_4$ than the same subjects before supplementation (FIG. 8). 20-OH $LTB_4$, 6-trans $LTB_4$ and 6-trans 12-epi $LTB_4$ levels were decreased to a similar degree after supplementation.

A final set of studies measured changes in the capacity of neutrophils to generate PAF ex vivo before and after GLA supplementation. Neutrophils of subjects receiving 3.0 g/day of GLA produced 40% less PAF after supplementation than neutrophil obtained from those same subjects before supplementation. Taken together, these data reveal that GLA supplementation can alter the capacity of neutrophils to generate lipid mediators. This inhibition appears to occur at some step distal to the phospholipase-catalyzed cleavage of AA from membrane phospholipids.

EXAMPLE 2

In Vitro Studies Examining the Metabolism of GLA in Human Neutrophils

Figure 10:
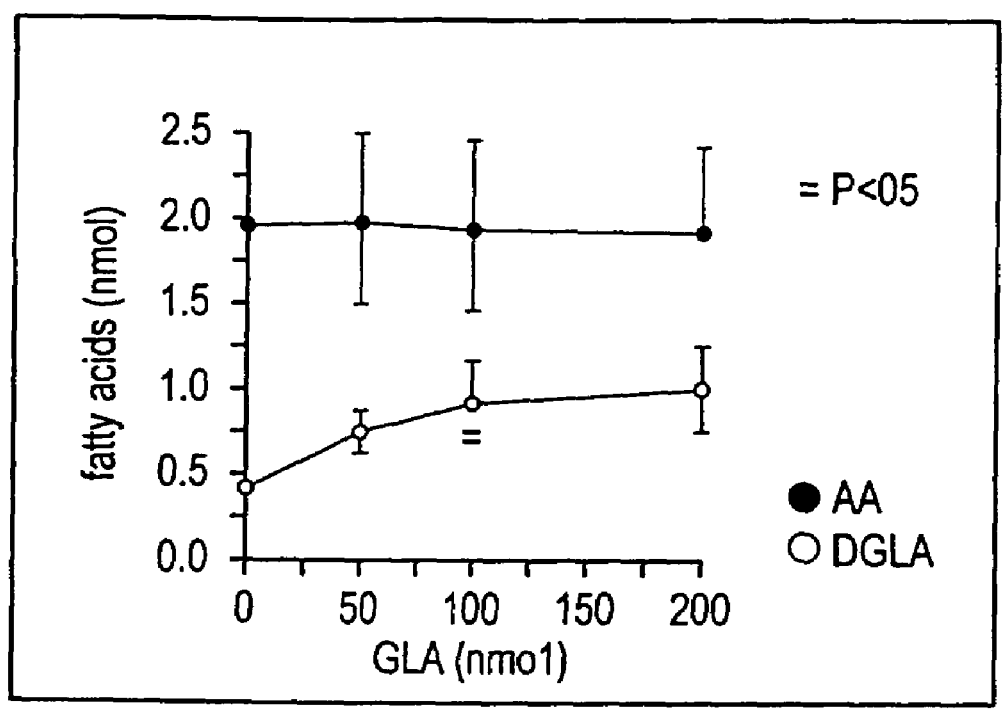
FIG. 10. In vitro metabolism of GLA in human neutrophils.

It is generally assumed that the liver has a key role in the in vivo elongation and desaturation of n-6 fatty acids. However, the role of other cells (especially inflammatory cells) and tissues has not been extensively studied. In addition, it is critical to evaluate the mechanism of leukotriene inhibition in less complex (than in vivo model) systems. To begin to address these problems, the inventor developed a model in which neutrophils could be incubated long-term with fatty acids or other fatty acid derivatives. Human neutrophils have been isolated and cultured overnight in RPMI, 2% insulin-transferrin and fetal bovine serum (FBS). In initial studies, varying concentrations of GLA (complexed to albumin) were provided to these cultured neutrophils for 24 h. FIG. 10 shows quantities of DGLA and AA in neutrophils at increasing concentrations of GLA. The quantity of DGLA in neutrophil glycerolipids increased as a function of the concentration of GLA. In contrast, there was no change in the quantity of AA in neutrophil phospholipids. These data revealed that neutrophils have the capacity to take up GLA and rapidly elongate it to DGLA. However, they do not desaturate DGLA to form AA. These data are consistent with in vivo findings that indicate that GLA supplementation leads to an increase in DGLA, but not GLA or AA in human neutrophil glycerolipid. Furthermore, they provide direct evidence that the neutrophils themselves can elongate GLA in vivo.

Figure 11:
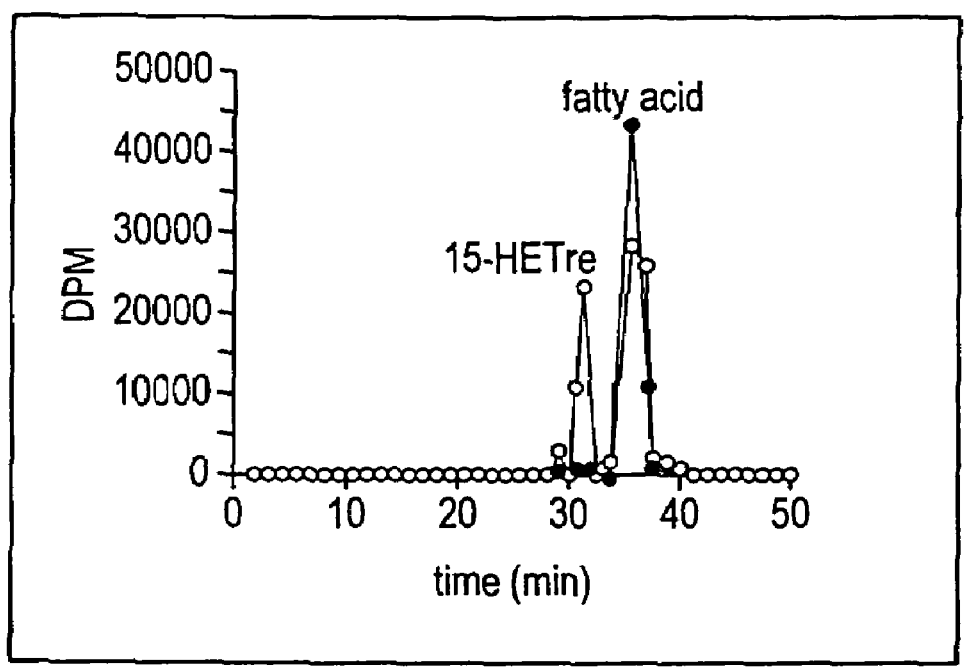
FIG. 11. Metabolism of $^{14}$C-DGLA to products by stimulated neutrophils.

It has been long recognized that arachidonate is hydrolyzed from membrane glycerolipids by phospholipase $A_2$ isotypes during cell stimulation. However, to date, there is little direct evidence that similar mechanisms exist to mobilize DGLA. To examine this question, neutrophils that had been cultured with varying concentrations of GLA (0 to 200 nmol) were stimulated with ionophore A23187, and mobilized fatty acids were measured by NICI GC/MS. DGLA along with AA were released from neutrophils during stimulation. To determine if neutrophils can further metabolize DGLA to oxygenated products, stimulated cells were provided [$^{14}$C]-DGLA and products were measured by reverse HPLC. Neutrophils primed with LPS followed by stimulation with FMLP also converted DGLA to 15 HETrE. FIG. 11 illustrates that A23187 stimulated neutrophils produce a labeled product that migrated with 15-HETrE. In contrast, none of this product was observed in unstimulated cells. To the inventor's knowledge, these are the first studies to demonstrate the capacity of neutrophils to release DGLA and convert it into oxygenated products.

Figure 12:
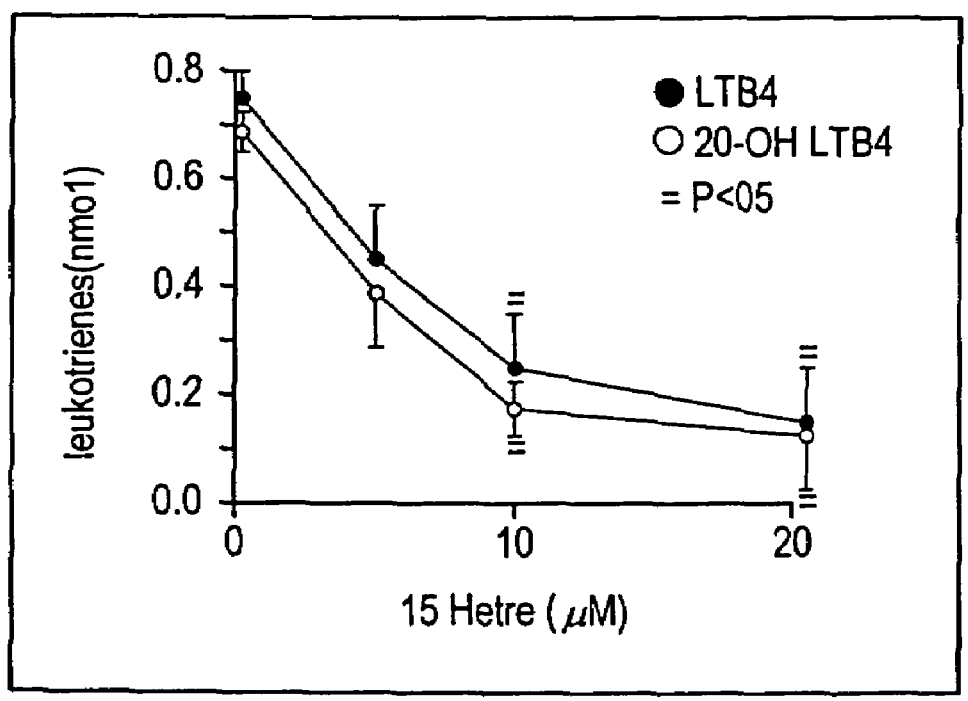
FIG. 12. Influence of 15-HETrE on leukotriene generation.

It is contemplated that neutrophils may also produce 8-hydroxy-9,11,14 eicosapentaenoic acid from DGLA. Borgeat and colleagues reported this to be a product of the incubation of dihomogammalinolenic acid with rabbit neutrophils. Studies were also designed to examine whether 15-HETrE produced by neutrophils might influence $LTB_4$ generation. Previous studies by Vanderhoek and colleagues have demonstrated that the AA product, 15-HETE, can reduce 5-lipoxygenase activity (Vanderhoek et al., *J. Biol. Chem.*, 255:10064–10066, 1980). Neutrophils were isolated from normal unsupplemented volunteers and were treated with various concentrations of 15-HETrE and then stimulated with ionophore A23187. FIG. 12 shows the generation of $LTB_4$ and its major metabolite 20-OH $LTB_4$ by stimulated neutrophils. 15-HETrE induced a dose dependent inhibition of leukotriene generation with an $IC_{50}$ of approximately 5 μM. In addition, DGLA at higher concentrations ($IC_{50}$, ~10 μM) also inhibited leukotriene generation. Although these studies do not prove that 15-HETrE or DGLA is the in vivo inhibitor of 5-lipoxygenase, they reveal that DGLA and oxygenated products of DGLA can potently influence eicosanoid generation.

EXAMPLE 3

Figure 13:
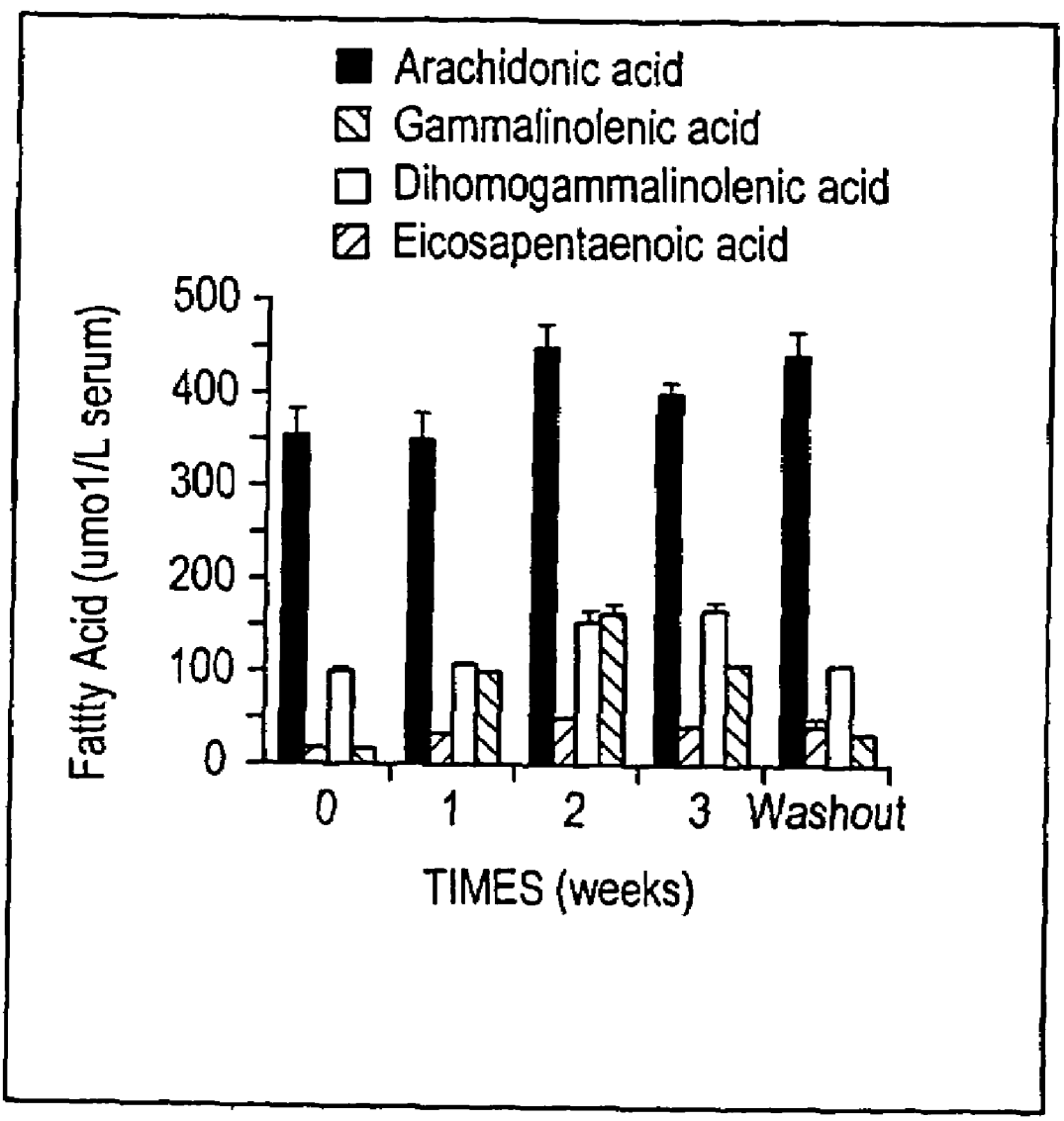
FIG. 13. In vitro metabolism of stearidonic acid in human neutrophils.

Influence of the Combination of GLA and Eicosapentaenoic Acid (EPA) on the Fatty Acid Composition of Serum and Neutrophil Lipids As mentioned above, a concern with the long-term effects of GLA supplementation is that there is an increase in serum levels of AA. There is a need, therefore, to find dietary strategies that will produce natural antagonist of AA in inflammatory cells without increasing serum AA. Previous in vitro studies in isolated hepatocytes and in vivo studies in animals suggest that EPA is a product inhibitor of the $\Delta^5$ desaturase (Gronn et al., *Biochim. Biophys. Acta*, 1125:3543, 1992; Dang et al., *Lipids*, 24:882–889, 1989). In order to determine whether EPA would perform a similar function in humans in vivo, three subjects on control diets (25% fat) were supplemented with a combination of EPA (1.5 g/day) and GLA (3.0 g/day) for three weeks. It was shown (FIG. 4 and FIG. 5) that this quantity of GLA (alone) induces marked increases in serum AA in both the short (3 weeks) and long term (12 weeks). The combination of GLA and EPA resulted in marked increases in GLA, DGLA and EPA in serum lipids. However, in contrast to the GLA supplementation alone, the combination of EPA with GLA did not cause an increase in serum AA (FIG. 13). These interesting results suggest that it may be possible to block the $\Delta^5$ desaturase in humans with EPA thereby providing a means to supplement humans with high levels of GLA without concomitant increases in serum AA levels.

EXAMPLE 4

Figure 14:
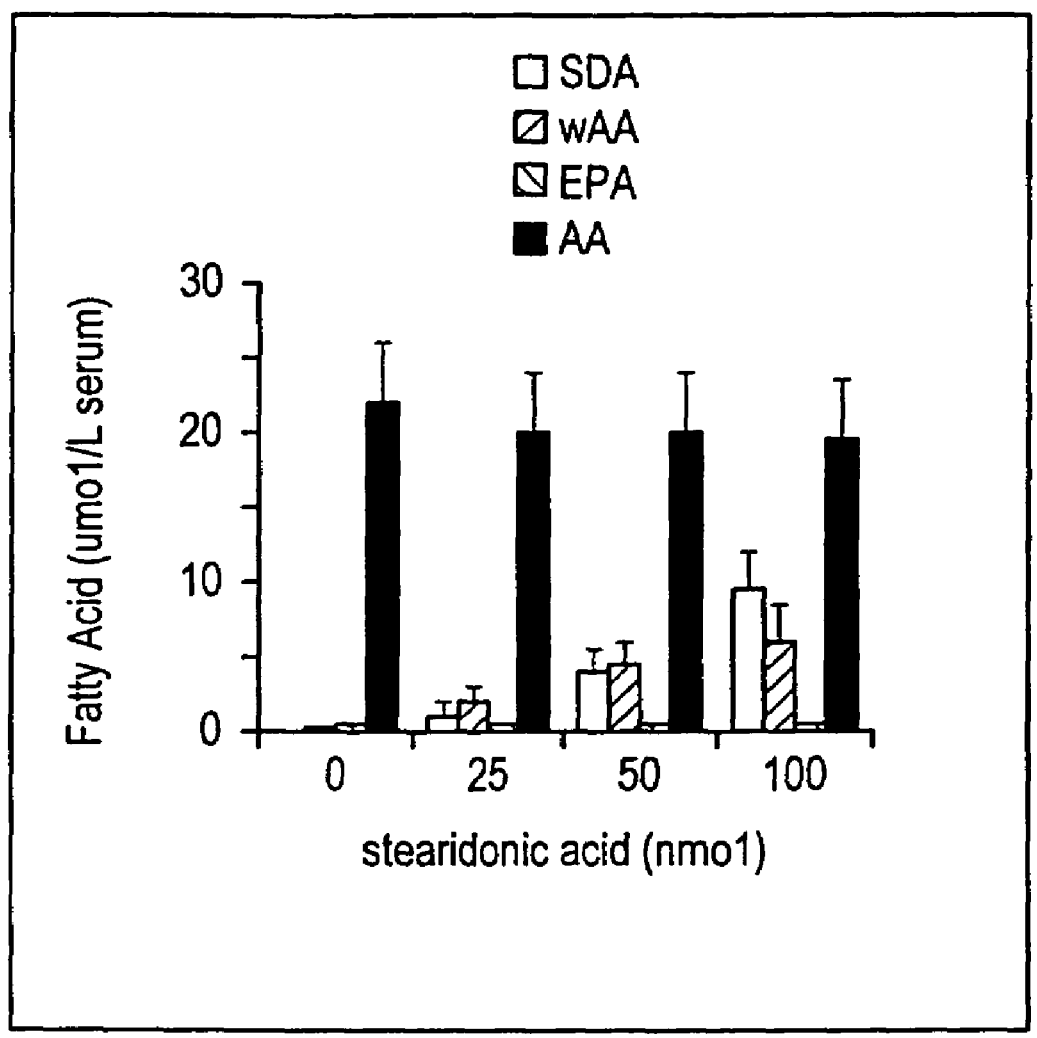
FIG. 14. In vitro metabolism of stearidonic acid in human neutrophils.

In Vitro Studies Examining the Metabolism of Stearidonic Acid in Human Neutrophils As described above, human neutrophils (in vitro in overnight culture) will take up GLA and elongate it to DGLA but not further desaturate that DGLA to AA. An alternative route to depleting AA in neutrophils may also be useful in modulating the inflammatory responses mediated by AA and its metabolites. It was contemplated that the n-3 fatty acid, stearidonic acid (18:4) would also be elongated in neutrophils to form $\omega$-3 arachidonic acid (FIG. 1). Varying concentrations of stearidonic acid were provided to cultured neutrophils for 24 h. Lipids were extracted and the quantities of fatty acids determined after base hydrolysis using GC/MS. There was no detectable ($\omega$-3 arachidonic acid in neutrophils before supplementation (FIG. 14). However, addition of stearidonic acid caused a dose-dependent increase in $\omega$-3 arachidonic acid in glycerolipids of these cells. In contrast to this increase, there was no increase in the $\Delta^5$ desaturase product of $\omega$-3 arachidonic acid, eicosapentaenoic acid, nor was there an increase in AA. Analogous to supplementation with GLA, these data reveal that neutrophils have the capacity to take up stearidonic acid and rapidly elongate it to $\omega$-3 arachidonic acid. However, they do not further desaturate $\omega$-3 arachidonic acid to form eicosapentaenoic acid.

These studies raise the interesting possibility that high levels of the AA analog, $\omega$-3 AA, can be induced in inflammatory cells by providing inflammatory cells (in vitro or in vivo) with stearidonic acid. Moreover, they point out the potential for ($\omega$-3 AA to compete with natural AA (n-6) for enzymes (phospholipase A2 isotypes, cyclooxygenase isotypes, and 5-lipoxygenase) that convert AA to oxygenated metabolites.

EXAMPLE 5

Development of a Model to Study the Influence of Diet on Clinical and Biochemical Parameters of Asthma Asthma presents a defined inflammatory disease that can be used as a model to test the efficacy of dietary manipulation. To this end an asthma model in humans was developed to test the reproducibility of the in vitro data and to determine the best dietary strategies. Another benefit of such a model is it allows the investigator to establish the effect of antigen challenge on AA levels in bronchoalveolar lavage fluid (BALF). Thus the present example teaches the use of an asthmatic model to test these parameters.

To this end, measures of airway physiology and analysis of BALF cellular and biochemical constituents were obtained from 5 stable atopic asthmatics before and after antigen challenge, both with and without prior corticosteroid therapy. A systemic corticosteroid arm was felt to be an impost to validate the physiologic variables as well as to ascertain which components in the BALF were sensitive markers of steroid-responsive inflammation. Additionally, AA levels were measured in BALF 4 h after inhaled antigen challenge (7 subjects) and at the time of the LAR (5 subjects). For comparison, identical BALF analyses were performed in ten normal volunteers (without antigen challenge or corticosteroids).

Study Design

Asthmatic subjects were defined using criteria proposed by the American Thoracic Society, *Am. Rev. Respir. Dis.*, 136:225–244, 1987. Normal subjects were healthy nonsmokers, without respiratory symptoms. In all subjects, demographic data, history and physical examination, baseline spirometry, skin testing and methacholine PC20, using a tidal breathing technique, were obtained after informed consent for study participation. This was followed, no earlier than 7 days later, by baseline bronchoscopy for collection of BALF. This concluded the study protocol for normal subjects.

In 5 subjects, inhaled antigen challenge was performed using a previously described protocol and physiologic data collected. Not less than 2 weeks later, PC20 was again determined and antigen challenge repeated with BALF collected at the time of the LAR as determined during the first challenge. Two to 4 weeks later, these subjects were placed on 40 mg of prednisone daily for 7 days. Inhaled antigen challenge was again performed and BALF obtained at the same time after antigen challenge as on the previous visit. In an additional 7 subjects, BALF was obtained 4 h after inhaled antigen challenge, but without a subsequent course of prednisone therapy.

Statistical Analysis

In the asthmatic patients, the changes in cell composition, eosinophil cationic protein (ECP), and protein in BALF among study conditions were examined using one way ANOVA with study period as the independent variable. If a significant interaction was found, a paired t-test was used to compare the means among test periods. Because the AA levels were not normally distributed within the groups, the non-parametric Wilcoxon signed-ranks test was used to analyze the differences in these measurements. A $p<0.05$ was used to determine statistical significance.

Results

Measures of airway response to antigen challenge were consistent and reproducible both immediately and at LAR. The mean time for LAR, was $6.4\pm1.5$ h after challenge. The mean (±SD) fall in $FEV_1$ immediately after antigen challenge was 35±8% while the fall at LAR was 28±18% from baseline $FEV_1$. Following prednisone, both the immediate response and LAR were ablated.

The percentages of neutrophils and eosinophils in BALF were significantly higher in the asthmatics. The level of ECP rose after antigen challenge and was suppressed by corticosteroid administration (p=0.03). While the percentage of eosinophils tended to mirror the changes in ECP, these changes did not achieve statistical significance. AA levels in BALF rose after antigen challenge (mean±SE: baseline=2.2±0.3 ng/ml BALF; post-challenge=3.9±1.0; p<0.05).

Discussion

This antigen challenge model of asthma provides reproducible physiologic (pulmonary function) data within and between subjects. Further, ECP appears to be a reproducible surrogate measure of eosinophil presence and/or activity in this model. In addition, AA levels can be observed to increase after antigen challenge in this model. Collectively, these measures offer the capability of assessing the efficacy of dietary manipulation with the expectation that significant differences among treatment regimens can be detected with a relatively small number of study subjects.

EXAMPLE 6

Figure 15:
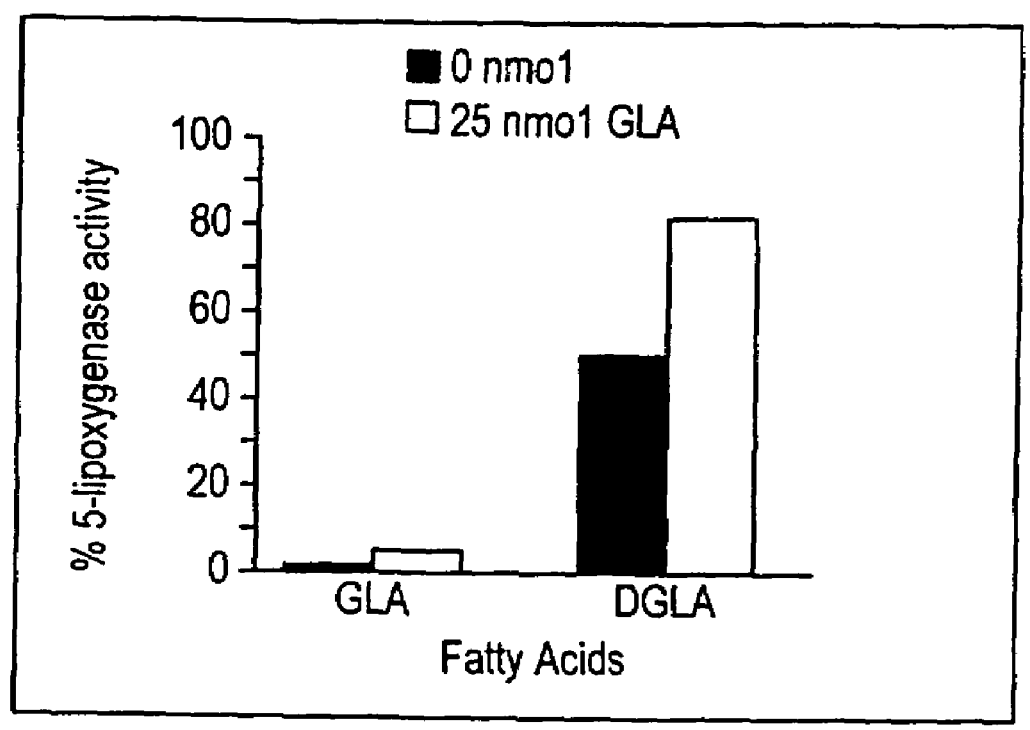
FIG. 15. Metabolism of GLA by human eosinophils.

Effect of GLA Supplementation on Eosinophil Fatty Acid Composition and Airway Functions An issue with the GLA data obtained with neutrophils is its relationship to atopic asthma and, in particular, whether the neutrophil has a key role in atopic asthma. While there is evidence that the neutrophil has a role in atopic asthma, previous studies, to date, point to the eosinophil as having a central role. Therefore, it was important to determine how GLA was metabolized by human eosinophils. Thus, eosinophils were isolated from atopic subjects and incubated with GLA as described above. Like the human neutrophils, supplementation of human eosinophils resulted in a marked increase in DGLA but no change in the quantity of AA in eosinophil glycerolipids (FIG. 15). These data reveal that eosinophils have the capacity to take up GLA and rapidly elongate it to DGLA. However, eosinophils do not further desaturate DGLA to form AA.

In a second set of studies, two atopic asthmatics were recruited and challenged with antigens as described above. In both subjects, the concentration of antigen necessary to drop $FEV_1$ by greater than 20% was established. At a subsequent date, they were each challenged with these respective concentrations of antigen and monitored with spirometry to assess the development of an early and late responses. Each of these subjects were then placed on GLA supplementation for four weeks and then challenged again with the same dose of antigen. The subjects were then placed back on their normal diets for two weeks and then challenged again with the same respective dose of antigen. The magnitude of the early response was diminished (when compared to pre- and post GLA supplementation) in both subjects four weeks after GLA supplementation. In contrast, GLA supplementation did not influence the late response.

Additionally, the influence of GLA supplementation in a human model of atopic asthma, on eicosanoid production, bronchial reactivity, and airway cellular influx can be measured as detailed herein. A random order, placebo-controlled crossover design preceded by a control diet "run in" phase study is performed. A crossover design is chosen to keep the number of subjects required for statistical validity as small as possible by minimizing the influence of intersubject variability with regards to the severity of asthma, environmental triggers and exposures, and nature and severity of the late asthmatic response (LAR). Subjects are studied after 3 weeks of a controlled "normal" diet with 25% of calories from fat, after 3 weeks of the "experimental" diet consisting of the "normal" diet supplemented with 4.5 grams (15 capsules/day) of GLA as borage oil, and after 3 weeks of a "placebo" diet consisting of the "normal" diet with 4.5 grams (15 capsules/day) of olive oil. Olive oil is 70% oleic acid, 13% C16, and 15% C18, (<1%, n-3) fatty acids as triglycerides. Neither oil supplement has either an odor or a taste when in capsule form. The experimental and placebo diets are given in random order. Each 3 week period is separated by a 4–6 week usual diet "washout" period when the diet of the study subjects is not controlled. Preliminary data from this group suggests that 4 weeks is a sufficient time period for abolition of an effect of diet during the preceding study period.

Results

It is contemplated that GLA supplementation and not placebo or "normal" diets will mitigate the response to antigen challenge as measured by the decrements in $FEV_1$ both immediate and the LAP, and reduce the influx of eosinophils into airways during the LAR. GLA supplementation will also likely attenuate antigen-induced urinary $LTE_4$ exertion and BALF AA increases.

While the antigen challenge model is capable of detecting a therapeutic effect due to prednisone with a small number of subjects, GLA supplementation may be associated with smaller, though significant, effects that are overlooked using relatively small sample sizes. The trial uses 10 subjects per group. Sample sizes are based on variance estimated and differences reported in the preliminary results. The contemplated sample sizes have a 90% power to demonstrate an effect on pulmonary function ($FEV_1$) that is at least half the magnitude observed with oral prednisone therapy in the pilot study, at an alpha of 0.05. Asthma is a complex disease process and it is possible that significant effects in some components may be missed by using a model that is not sensitive to these effects. For example, an antigen challenge model would not be the appropriate system in which to detect an impact on neurally-mediated immediate processes (e.g., airway cooling). The effect of GLA supplementation, would, however, suggest that this antigen challenge model is appropriate.

EXAMPLE 7

Dietary Strategies in Humans Utilizing Endogenous Elongase Activity within Inflammatory Cells to Synthesize Structural Analogs of AA from Dietary Precursors Without Concomitantly Increasing Levels of Circulating AA The data suggest there may be two strategies that can be utilized in humans to synthesize analogs of AA in inflammatory cells without concomitant increases in serum AA. The first approach (FIG. 16A) is to supplement the diets of humans with a combination of gammalinolenic acid (GLA) and a $\Delta^5$ desaturase inhibitor such as eicosapentaenoic acid (EPA), for example. This strategy is based on in vitro data in hepatocytes and in vivo data in animals which indicate that EPA is a product inhibitor of the enzyme activity that synthesizes it, the $\Delta^5$ desaturase (Gronn et al., 1992; Dang et al., 1989). The inventor has shown in two volunteers that administering of GLA in combination with EPA will induce a marked accumulation of DGLA in circulation and neutrophil lipids without causing a marked accumulation of AA in serum lipids (which is seen with GLA supplementation in the absence of EPA).

If in vivo administration of EPA is an effective means to block the hepatic $\Delta^5$ desaturase, this combination should furnish a means to provide high concentrations of GLA to humans to synthesize the close structural analog of AA, DGLA, in inflammatory cells. This will have the action of inhibiting AA metabolism and eicosanoid biosynthesis, and attenuating signs and symptoms of inflammatory disorders, without the significant side effect of the accumulation of AA in circulation.

The second approach involves administering the n-3 fatty acid, stearidonic acid, to humans (FIG. 16B). This fatty acid is converted (by the endogenous elongase in inflammatory cells) to a structural analog of AA, ($\omega$-3 AA and this product will block AA metabolism and thus have anti-inflammatory effects. There have been several studies over the last few years that have examined the effects of in vivo supplementation with alpha linolenic acid (18:3, n-3) in both humans and animals. Generally, these studies have shown that alpha linolenic acid has only modest anti-inflammatory effects (Nordstrom et al., *Rheumatol. Int.*, 14:231–234, 1995; Larsson-Backstrom et al., *Shock*, 4:11–20, 1995; Clark et al., *Kidney Int.*, 48:475–480, 1995; Shoda et al., *J. Gastroenterol.*, 30(suppl 8):98–101, 1995). However, only a very small portion of alpha linolenic acid is converted to stearidonic acid by the $\Delta^6$ desaturase. In fact, this step appears to be the rate-limiting step in n-3 polyunsaturated fatty acid biosynthesis. As described herein, stearidonic acid supplementation is an efficacious means to block AA metabolism because it bypasses the rate-limiting step ($\Delta^6$ desaturase) and is directly utilized by inflammatory cell elongase activity. A major advantage of stearidonic acid verse GLA (alone) as a supplement is that the elongation/$\Delta^5$ desaturase product from this precursor is EPA and not AA. Consequently even if EPA accumulates in serum components, it will not have the potential detrimental effects of AA.

EXAMPLE 8

Inhibition of Delta-5 Desaturase by Eicosapentaenoic Acid in Human Liver Cells

The use of $\Delta^5$ desaturase inhibitors in the practice of the present invention rests, in certain aspects, on the ability of those inhibitors to affect $\Delta^5$ desaturase activity in the hepatic cells of a subject who is receiving GLA or DGLA as a dietary supplement, or especially as a treatment for an inflammatory disorder or condition, for example. As is described elsewhere herein, the DGLA, if taken up by liver cells, or GLA that has been elongated to DGLA undergoes $\Delta^5$ desaturation in hepatic cells to produce arachidonic acid. This desaturation does not occur in immune system cells such as neutrophils, which lack the $\Delta^5$ desaturase activity.

Figure 17A:
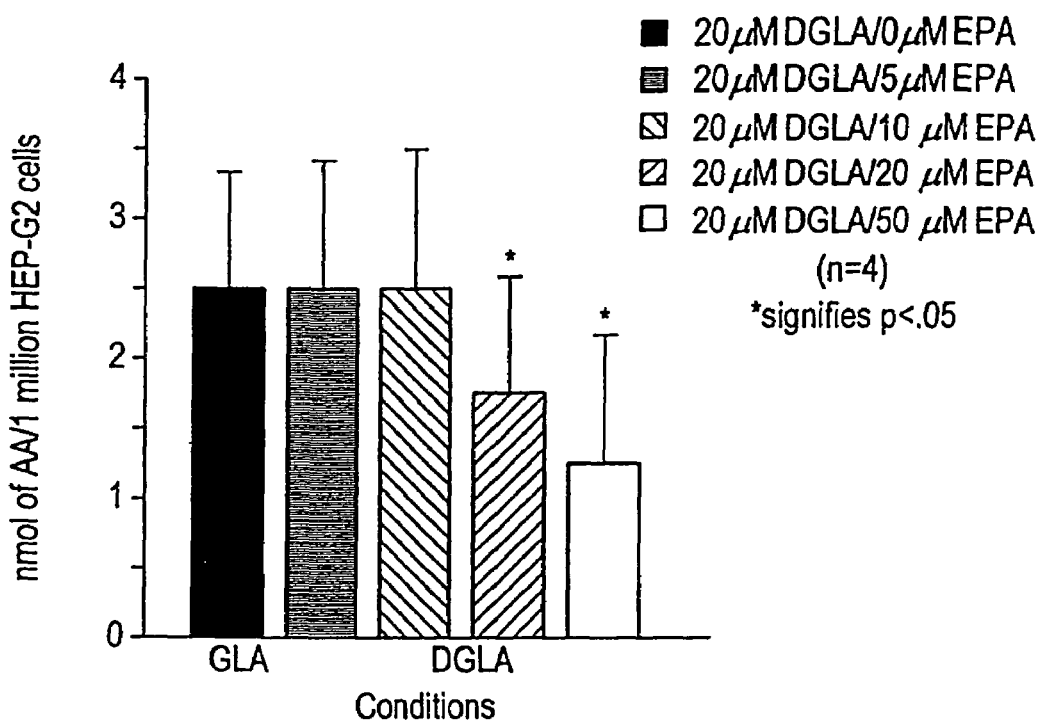
FIG. 17A. Bar graph indicating inhibition of arachidonic acid synthesis in liver cells by $\Delta^5$ desaturase inhibitor, eicosapentaenoic acid.
Figure 17B:
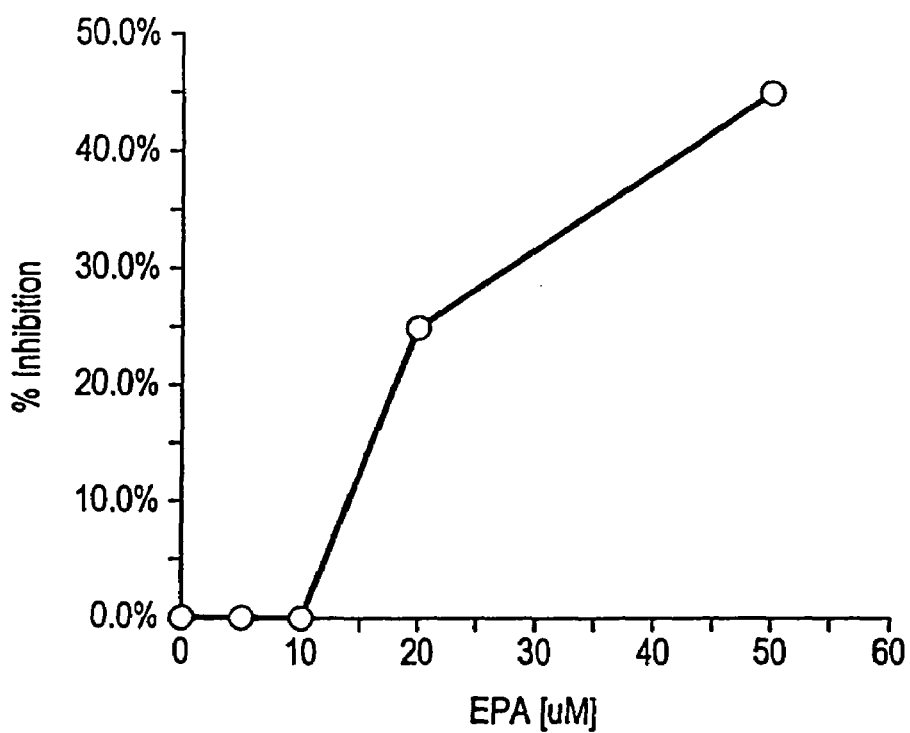
FIG. 17B. Percent inhibition of arachidonic acid synthesis in liver cells by $\Delta^5$ desaturase inhibitor, eicosapentaenoic acid.

In order to demonstrate that an inhibitor such as eicosapentaenoic acid has the capacity to block $\Delta^5$ desaturase, various concentrations of EPA were added exogenously, along with DGLA, to a human liver cell line, HEP-G2, and the conversion of DGLA to AA was monitored. The results are shown in FIGS. 17A and 17B. The data indicate that EPA caused a dose-dependent inhibition of DGLA conversion to AA with a maximum of 50% inhibition at 50 µM. This study illustrates the effectiveness of adding a $\Delta^5$ desaturase inhibitor in conjunction with GLA in order to reduce serum arachidonic acid.

EXAMPLE 9

Determination of the Accumulation of $\omega$-3 AA from Stearidonic Acid Treatment of Neutrophils Affects the Capacity of Cells to Release AA and Synthesize Eicosanoids In additional work, the inventor has also demonstrated that human neutrophils rapidly take up stearidonic acid (18:4, n-3) and convert it to $\omega$-3 AA. $\omega$-3 AA is a 20 carbon fatty acid that is a close structural analog of AA (n-6). Thus, $\omega$-3 AA may also serve as a competitive antagonist for AA (n-6) during AA metabolism. The following examples provide details of procedures used to investigate this strategy.

It is not known whether $\omega$-3 AA-containing phospholipids will influence the capacity of $PLA_2$ isotypes to release AA (n-6) in stimulated neutrophils or whether $\omega$-3 AA will effect enzymes distal to phospholipase $A_2$ such as 5-lipoxygenase or cyclooxygenase I and II. These issues are readily explored by 'loading' human neutrophils in vitro with $\omega$-3 AA; and then activating the cells.

The capacity of the cells to release AA, stearidonic acid, and $\omega$-3 AA, as well as produce eicosanoids, is examined.

Isolated neutrophils (20 million/40 ml of media) or eosinophils (10 million/40 ml of media) are maintained in culture with RPMI, 2% insulin transferrin, 1% FBS and various concentrations of stearidonic acid (quantities ranging from 0 to 200 nmol). After 24 h, these cells are washed (2×) with Hanks Balanced Salt Solution containing 0.25 mg/ml albumin and then resuspended at a concentration of 10 million/ml. Cells then are stimulated with ionophore A23187 (1 µM) and maintained at 37° C. for an additional 5 min. For a more physiologic stimulus, neutrophils are incubated in 10% autologous plasma containing 1 µg/ml LPS for 30 min. Eosinophils are stimulated with PAF (1 µM). Cells are then washed and incubated with or without FMLP (1 µM). Reactions are terminated with methanol/chloroform (2:1, v/v) or methanol, for fatty acid release or leukotriene analysis, respectively.

To determine the quantity of fatty acids released from glycerolipids during cell activation, octadeuterated AA and trideuterated stearic acid are added as internal standards to the terminated reaction mixture and lipids are extracted by the method of Bligh and Dyer, 1959. Fatty acids in samples are then analyzed by NICI GC/MS. Quantities of leukotrienes are determined following reverse phase HPLC separation as described above. Quantities of prostaglandins are determined by NICI GC/MS. From these studies, it can be determined: 1) Whether the presence of $\omega$-3 AA or stearidonic acid-containing phospholipid in cellular membranes of neutrophils and eosinophils influence the capacity of neutrophil phospholipase $A_2$(s) to mobilize AA (n-6); 2) Whether $\omega$-3 AA or stearidonic acid is released from membrane glycerolipids during cell activation; and 3) Whether the presence of $\omega$-3 fatty acids affects the capacity of neutrophils and eosinophils to synthesize leukotrienes and prostaglandins.

In addition to examining the effect of $\omega$-3 arachidonic acid on AA metabolism, it is also determined whether $\omega$-3 arachidonic acid itself is metabolized by neutrophils to eicosanoid-like products. In these studies, A23187-stimulated and unstimulated neutrophils are incubated with $\omega$-3 arachidonic acid (from 1 to 50 µM for 10 min.). Products are then separated by reverse phase HPLC and fractions monitored at 234 nM [HETE-like compounds] or 270 [leukotriene-like compounds]. New products observed with $\omega$-3 AA and A23187 addition (not observed with either alone) are isolated and converted to methoxime-pentafluorobenzylester-trimethylsilyl ether derivatives as described previously. Derivatized products as carboxylate anions are analyzed by negative ion chemical ionization GC/MS. It is possible that some products of ω-3 AA may not absorb at the above mentioned wavelengths. In this case, there are several HPLC-electrospray mass spectrometry/mass spectrometry procedures for characterizing the double bond positions and position of hydroxyl modifications of fatty acids. These are used to definitively identify products from ω-3 AA.

It is likely that ω-3 AA attenuates the capacity of cells to synthesize leukotrienes. Further, neutrophil $PLA_2(s)$ hydrolyzes ω-3 AA from cellular glycerolipids during cell activation.

EXAMPLE 10

Effects of In Vivo Supplementation with Oils Enriched in Stearidonic Acid (18:4, n-3) on the Quantities and Ratios of n-6 and n-3 Fatty Acid in Serum and Neutrophil Lipids and the Ex Vivo Capacity of Stimulated Neutrophils from Supplemented Volunteers to Release Fatty Acids and Produce Eicosanoids It has been demonstrated that in vitro incubation (for 24 h) of stearidonic acid with human neutrophils leads to a dramatic increase in the quantity of ω-3 AA in cellular glycerolipids and thus a large increase in the ω-3 AA/AA ratio in these complex lipids. These data indicate that the neutrophil elongase activity can be utilized to synthesize close structural analogs of AA from appropriate dietary precursors. These analogs are then postulated to affect AA metabolism via phospholipase $A_2$, 5-lipoxygenase or cyclooxygenase I or II.

It is contemplated that there is an in vivo dose-dependent relationship between the quantity of stearidonic acid consumed in diets and the quantities of stearidonic acid, ω-3 AA and eicosapentaenoic acid in serum lipids and ω-3 AA in neutrophil lipids. If ω-3 AA accumulates in neutrophil lipids as predicted and it acts as a competitor with AA (n-6), then it is also likely that increasing stearidonic acid doses will correlate with a further attenuation of leukotriene generation by neutrophils and whole blood, and a concomitant increase in ω-3 AA release from cellular phospholipids.

Recruitment of subjects, diet preparations and monitoring diet compliance are all performed as described above. To limit variability of volunteers' normal diets, four randomly assigned groups of volunteers (10 per group, 5 males and 5 females) are provided identical 25% fat diets for two weeks before starting stearidonic acid (SDA) supplementation. Then one group of volunteers consumes 1.5 g SDA/day; another group consumes 3.0 g SDA/day and a third group consumes 6.0 g SDA/day. A separate (fourth) group of subjects consumes 3.0 g of alpha linoleic acid from Crossential GLA. Crossential GLA is a commercially available oil from Croda which contains >75% of its fatty acids as alpha linolenic acid. This oil contains no stearidonic acid. This control is necessary to test the hypothesis that bypassing the $\Delta^6$ desaturase is necessary to effectively produce analogs of AA (ω-3 AA) in inflammatory cells. All groups consume their respective supplement and identical controlled 25% diets for four weeks. Fasting blood is collected before starting the 25% diet (before diet control) and one and seven days before starting the supplementation. Subsequently, fasting blood samples are collected every 7 days after supplementation and 2 weeks after supplementation has ceased.

Analysis of Fatty Acids and Eicosanoids in Neutrophils and Whole Blood

Fasting (12 h) blood samples are obtained at each of the time points (in all protocols) described above. The following fatty acid and eicosanoid measurements are made at each time point. Eicosanoid measurements in whole blood and in stimulated neutrophils are performed as described above.

Measurements of Free AA, ω-3 AA and Stearidonic Acid in Stimulated Neutrophils

Stimulated neutrophils release AA from phospholipids utilizing $PLA_2(s)$ reactions. It is also possible that $PLA_2(s)$ recognizes ω-3 AA or SDA-containing phospholipids, or supplementation with SDA blocks the $PLA_2$-induced release of AA in neutrophils. Therefore, free AA, (ω-3 AA, SDA, and eicosapentaenoic acid are measured by NICI GC/MS before and after stimulation of neutrophils isolated from each volunteer at each dietary time point. Neutrophils are stimulated with ionophore A23187, LPS or LPS and FMLP.

It is expected that stearidonic acid (like GLA) is both elongated and $\Delta^5$ desaturated in serum compartments to form ω-3 AA and eicosapentaenoic acid (EPA), respectively. It is also contemplated that only ω-3 AA accumulates in neutrophil glycerolipids, thus increasing the ω-3 AA/AA ratio. Stearidonic acid containing oils are also expected to induce much higher quantities of ω-3 AA in neutrophil lipids than alpha linolenic acid. It is likely that the accumulation of ω-3 AA translates into a reduction in the capacity of blood cells, the neutrophil in particular, to produce eicosanoids. Again, one of the major advantages of stearidonic acid versus GLA as a supplement is that the elongation/$\Delta^5$ desaturase product from this precursor is EPA and not AA. Consequently, even if EPA accumulates in serum components, it will not enhance AA metabolism.

EXAMPLE 11

A Preferred Embodiment of a Dietary Fatty Acid Supplement

A preferred composition would be a stabilized emulsion that can be consumed neat or easily mixed in a drink or yogurt. The preferred composition of the emulsion would be:

| Constituents | Weight (g) |
| --- | --- |
| Purified water | 19.29 |
| Ascorbyl palmitate | 0.2 |
| Sorbic acid | 0.16 |
| Sucrose | 25 |
| Glycerin | 5 |
| Xanthan gum | 0.3 |
| Concentrated borage oil (40% GLA) | 20 |
| Concentrated marine oil (33% EPA) | 15 |
| Flavor (orange/peach) | 15 |
| Colorant (orange) | 0.05 |
| Total | 100 |

The composition is preferably packaged in an oxygen-free environment in single daily dosage packages made of oxygen impermeable materials such as foil-lined pouches. The recommended daily dosage of 20 grams per day would deliver about 1.5 grams of gammalinolenic acid and about 1.0 gram of eicosapentaenoic acid per day. The formulations preferably contain natural anti-oxidants, natural fruit flavors and natural coloring agents. The stabilized emulsion also may contain a natural sweetener and natural preservative.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A liquid dietary supplement consisting essentially of:
   19.29 weight percent water;
   25 weight percent sucrose;
   35 weight percent oils;
   15 weight percent flavoring;
   5 weight percent glycerin; and
   less than 1 weight percent minor ingredients selected from antioxidants, preservatives, colorants, stabilizers, emulsifiers or a combination thereof; wherein the oils are (i) concentrated borage oil and (ii) concentrated marine oil that contains eicosapentaenic acid.

2. The dietary supplement of claim 1, wherein the oils consist of 57% concentrated borage oil and 43% concentrated marine oil.

3. The dietary supplement of claim 1, wherein the flavoring is orange/peach flavor.

4. The dietary supplement of claim 1, wherein the stabilizer is xanthan gum, the preservative is sorbic acid and the antioxidant is ascorbyl palmitate.

* * * * *